(12) United States Patent
Tachedjian et al.

(10) Patent No.: US 9,801,839 B2
(45) Date of Patent: Oct. 31, 2017

(54) THERAPEUTIC METHOD

(71) Applicant: Macfarlane Burnet Institute for Medical Research and Public Health Pty Ltd, Melbourne, Victoria (AU)

(72) Inventors: Gilda Tachedjian, Malvern East (AU); Anna Hearps, Windsor (AU)

(73) Assignee: Macfarlane Burnet Institute for Medical Research and Public Health Pty Ltd, Melbourne (AU)

( * ) Notice: Subject to any disclaimer, the term of this patent is extended or adjusted under 35 U.S.C. 154(b) by 126 days.

(21) Appl. No.: 14/634,691

(22) Filed: Feb. 27, 2015

(65) Prior Publication Data

US 2015/0306053 A1    Oct. 29, 2015

(30) Foreign Application Priority Data

Feb. 28, 2014 (AU) ................................ 2014900673

(51) Int. Cl.
*A61K 31/19* (2006.01)
*A61K 9/06* (2006.01)
*A61K 47/10* (2017.01)
*A61K 9/00* (2006.01)

(52) U.S. Cl.
CPC ............ *A61K 31/19* (2013.01); *A61K 9/0034* (2013.01); *A61K 9/06* (2013.01); *A61K 47/10* (2013.01)

(58) Field of Classification Search
None
See application file for complete search history.

(56) References Cited

PUBLICATIONS

Decena, et al., J. Obstet. Gynaecol. Res., 32:243 (Apr. 2006).*
Alexander et al., "Bacterial lipopolysaccharides and innate immunity," J Endotoxin Res, 7(3):167-202, (2001).
Blaskewicz et al., "Structure and function of intercellular junctions in human cervical and vaginal mucosal epithelia," Biol Reprod, 85:97-104, (2011).
Fichorova et al., "Differential expression of immunobiological mediators by immortalized human cervical and vaginal epithelial cells," Biol Reprod, 60:508-514, (1999).
Hickey et al., "Innate and adaptive immunity at mucosal surfaces of the female reproductive tract: stratification and integration of immune protection against the transmission of sexually transmitted infections," J Reprod Immunol, 88:185-194, (2011).
Kaushic, "HIV-1 infection in the female reproductive tract: role of interactions between HIV-1 and genital epithelial cells," Am J Reprod Immunol, 65:253-260, (2011).
Keller et al., "Phase I randomized safety study of twice daily dosing of acidform vaginal gel: Candidate antimicrobial contraceptive," Plos One, 7:e46901, (2012).
Mirmonsef et al., "Short-chain fatty acids induce pro-inflammatory cytokine production alone and in combination with toll-like receptor ligands," Am J Rep Immunol, 67:391, (2012).
Mossop et al, "Influence of lactic acid on endogenous and viral RNA-induced immune mediator production by vaginal epithelial cells," Obstet Gynecol, 118:840-846, (2011).
Pudney et al, "Anderson. Immunological microenvironments in the human vagina and cervix: mediators of cellular immunity are concentrated in the cervical transformation zone," Biol Reprod, 73:1253-1263, (2005).
Ulevitch et al, "Recognition of gram-negative bacteria and endotoxin by the innate immune system," Curr Opin Immunol, 11:19-22, (1999).
Wira et al, "Epithelial cells in the female reproductive tract: a central role as sentinels of immune protection," Am J Reprod Immunol, 53:65-76, (2005).

* cited by examiner

*Primary Examiner* — Michael Barker
(74) *Attorney, Agent, or Firm* — Alston & Bird LLP

(57) ABSTRACT

The present invention relates generally to a method of down-regulating an inflammatory response in a mammal and to agents useful for same. More particularly, the present invention relates to a method of down-regulating an inflammatory response in the reproductive tract or external genital tissue of a female mammal by contacting the mucosal tissue of the reproductive tract and/or genitalia with lactic acid and to agents useful for same. The method of the present invention is useful, inter alia, in the treatment and/or prophylaxis of conditions characterised by an aberrant, unwanted or otherwise inappropriate inflammatory response including, for example, atrophic vaginitis, irritant vaginitis or infectious vaginitis.

15 Claims, 17 Drawing Sheets

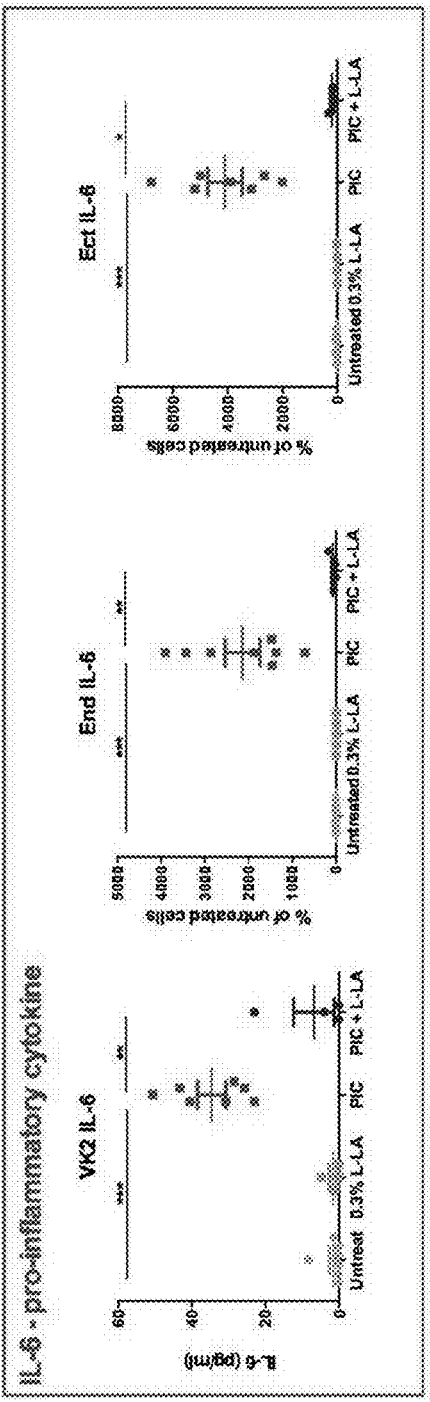
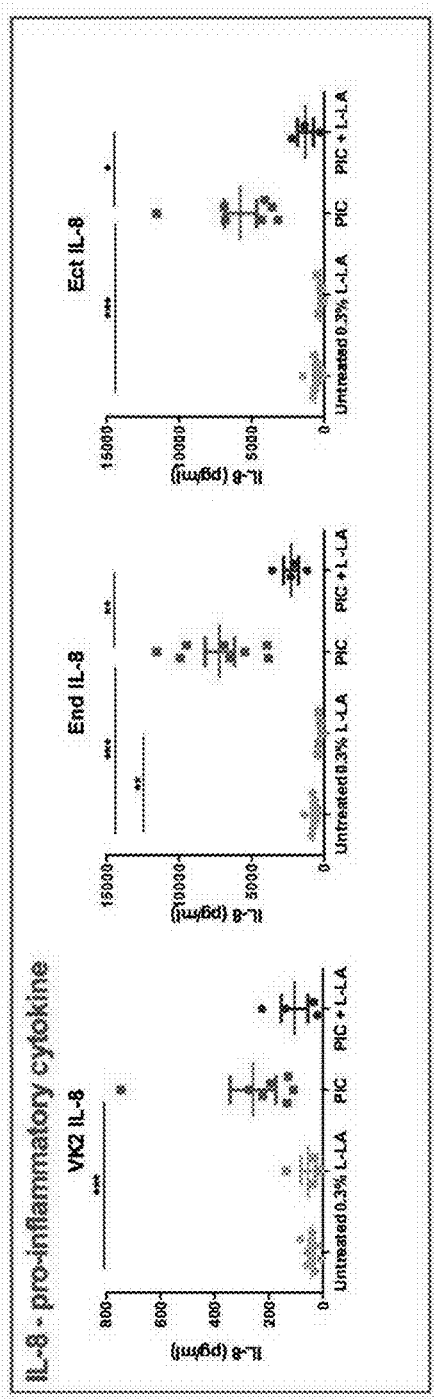
FIG. 4A
FIG. 4B

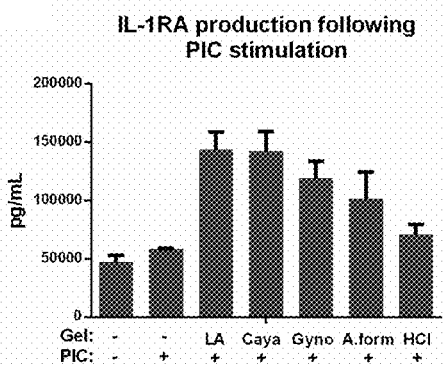
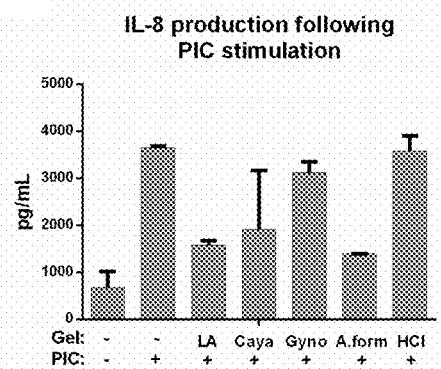
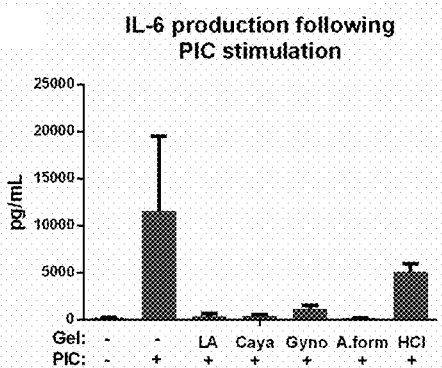
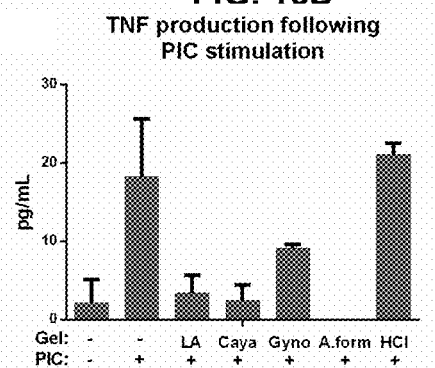
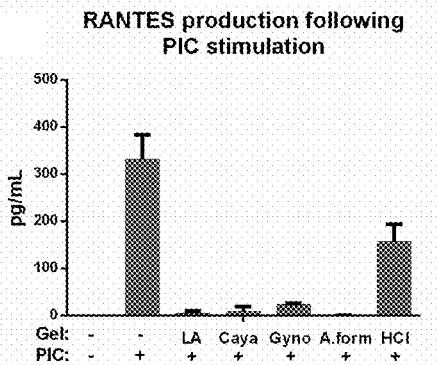
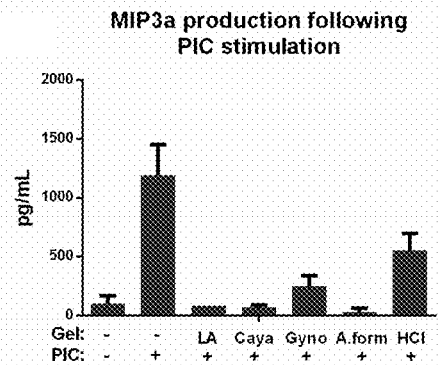

THERAPEUTIC METHOD

CROSS REFERENCE TO RELATED APPLICATION

The present application is a non-provisional of AU 2014900673 filed Feb. 28, 2014, which is incorporated by reference in its entirety for all purposes.

FIELD OF THE INVENTION

The present invention relates generally to a method of down-regulating an inflammatory response in a mammal and to agents useful for same. More particularly, the present invention relates to a method of down-regulating an inflammatory response in the reproductive tract or external genital tissue of a female mammal by contacting the mucosal tissue of the reproductive tract and/or genitalia with lactic acid and to agents useful for same. The method of the present invention is useful, inter alia, in the treatment and/or prophylaxis of conditions characterised by an aberrant, unwanted or otherwise inappropriate inflammatory response including, for example, atrophic vaginitis, irritant vaginitis or infectious vaginitis.

BACKGROUND TO THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

Mammals are required to defend themselves against a multitude of pathogens including viruses, bacteria, fungi and parasites, as well as non-pathogenic insults such as tumours and toxic, or otherwise harmful, agents. In response, effector mechanisms have evolved which are capable of mounting a defence against such antigens. These mechanisms are mediated by soluble molecules and/or by cells.

In the context of these effector mechanisms, inflammation is a complex multifaceted process in response to disease or injury and which is regulated by the release of a series of cytokines (Alexander et al, 2001, *J Endotoxin Res* 7:167-202). These cytokines are classified in general terms as pro-inflammatory or anti-inflammatory cytokines and the critical balance between release and activity of cytokines with opposing actions regulates the inflammatory response to prevent it from becoming overt or understated.

If the inflammatory response continues unchecked and is overt then the host may suffer associated tissue damage and in severe cases this may present as septic shock and multi-organ failure can occur (Ulevitch et al., 1999, *Curr Opin Immunol* 11:19-22). Conversely, a poor or understated inflammatory response may mean uncontrolled infection resulting in chronic illness and host damage. Regulation of the inflammatory response is important at both the systemic level and the local level.

The discovery of the detailed processes of inflammation has revealed a close relationship between inflammation and the immune response. There are five basic indicators of inflammation, these being redness (rubor), swelling (tumour), heat (calor), pain (dolor) and deranged function (functio laesa). These indicators occur due to extravasation of plasma and infiltration of leukocytes into the site of inflammation. Consistent with these indicators, the main characteristics of the inflammatory response are therefore:

(i) vasodilation—widening of the blood vessels to increase the blood flow to the infected area;
(ii) increased vascular permeability—this allows diffusible components to enter the site;
(iii) cellular infiltration—this being the directed movement of inflammatory cells through the walls of blood vessels into the site of injury;
(iv) changes in biosynthetic, metabolic and catabolic profiles of many organs; and
(v) activation of cells of the immune system as well as of complex enzymatic systems of blood plasma.

The degree to which these characteristics occur is generally proportional to the severity of the injury and/or the extent of infection.

In the context of the unique microenvironment of the human female reproductive tract, the mucosal epithelium of the reproductive tract acts as a physical barrier and expresses immunological mediators that serve as the first line of attack against infection (Hickey et al, 2011, *J Reprod Immunol* 88:185-194; Kaushic, C. 2011, *Am J Reprod Immunol* 65:253-260. The vagina and ectocervix comprise multiple layers of usually non-keratinized stratified squamous epithelium, with the uppermost permeable stratum corneum layer lacking tight junctions (Blaskewicz, et al. 2011, *Biol Reprod* 85:97-104), and are in contact with vaginal microbiota and semen. The cervical transformation zone separating the endocervix and ectocervix is the most immunologically active site in the reproductive tract with a relative abundance of lymphocytes and antigen presenting cells (Pudney, et al. 2005. *Biol Reprod* 73:1253-1263). Additionally, the vagina/ectocervix and endocervix exhibit immunological functions by conferring tolerance to microbes, maintaining epithelial integrity and recruiting and supporting of immune cells (Fichorova, R. N., and D. J. Anderson. 1999. *Biol Reprod* 60:508-514). As the front line of the innate immune response, reproductive tract epithelial cells express Toll-like receptors (TLRs) (Kaushic, C. 2011. Supra; Wira, et al. 2005. *Am J Reprod Immunol* 53:65-76). They respond to pathogen associated molecular patterns (PAMPs) via their TLRs by secreting cytokines and chemokines, antimicrobial peptides (defensins and secretory leukocyte peptidase inhibitor; SLPI), antimicrobial enzymes (lactoferrin and lysozome), surfactant protein A and complement (Fichorova, R. N., and D. J. Anderson. 1999. Supra; Hickey, et al. 2011, Supra; Kaushic, C. 2011, Supra). Nevertheless, disruption in the equilibrium of the reproductive tract, leading to the onset of inflammation is experienced by many women. The consequences of disturbances in this microenvironment range from annoying irritation through to an increased susceptibility to serious infections, such as HIV. To this end, three of the main causes of vaginal inflammation are:

(i) Atrophic vaginitis—This is most likely to be the result of having had a hysterectomy or occurs in a post menopausal woman. Atrophic vaginitis is estimated to affect as many as 40% of women. This type of inflammation is brought about due to the lack of estrogen stimulation of the vaginal tissue which can lead to the formation of adhesions, painful intercourse and an increased susceptibility to infections, itching burning, stinging and a watery discharge.
(ii) Irritant vaginitis—Irritant vaginitis is caused by an irritant. For example, sensitivity to a chemical being used or an allergic reaction to something one has come into contact with. This can be caused by a number of chemicals or physical agents, including tampons, the chemicals in scented feminine hygiene products, of personal lubricant, or even the harshness of the chemicals in the detergent being used to wash ones undergarments.

(iii) Infectious vaginitis—Infectious vaginitis is any type of vaginitis caused by microorganism infection—fungal, bacterial, viral, parasitic or otherwise. These include gardeneralla (a bacterial infection), any type of virus, STDs (like *chlamydia*, gonorrhea, or trichomoniasis), and vaginal yeast infection.

Although *Lactobacillus* sp dominate the microbiota of the healthy female reproductive tract and produce lactic acid (both L and D isoforms) to a concentration of approximately 1% which acidifies the reproductive tract to pH<4, the role, if any, of *Lactobacillus* sp., amongst the many other flora present in the reproductive tract, in terms of contributing to the health of the reproductive tract, has not been understood. That is, the vaginal microbiome is complex.

In fact, whereas *Lactobacillus* sp. have been shown to be associated with anti-inflammatory activity in the gut, the studies of Mossop et al (2011, *Obstet. Gynecol.* 118:840-6) demonstrated that with human female reproductive tissue, lactic acid, this being the major metabolite produced by *Lactobacillus* sp., is pro-inflammatory at low pH. This finding is not unexpected when one considers that the human female reproductive tract is a unique microenvironment. Specifically, the vagina is a highly acidic environment, more so than other organs or tissue. In fact, the human female reproductive tract is significantly more acidic than even the reproductive tracts of other non-human primates. Still further, it is known that carboxylic acids, such as acetic acid, and short chain fatty acids produced by bacterial vaginosis-associated bacteria are pro-inflammatory (Mirmonsef et al 2012, *Am J Rep Immunol* 67: 391). Again, this contrasts to the situation in the gut where the same carboxylic acids and short chain fatty acids are shown to exhibit anti-inflammatory effects.

Although lactic acid is included in the formulations of a range of vaginal gels which are currently on the market, in some of these gels it is included merely as an excipient. That is, as a largely inactive substance used as a vehicle for the active ingredient in the gel, this usually being a microbicide. In fact, the lactic acid in these formulations is used at a concentration significantly higher than the physiological concentrations present in the human vagina. Nevertheless, lactic acid is known to conveniently function as a preservative. Still further, since it is a naturally acid molecule, in some gels, although not used strictly as an excipient, it is included for its role in acid buffering in the presence of semen to kill sperm.

In fact, Acidform, an acid-buffering product, which inactivates spermatozoa, is formulated with 2% lactic acid and other acids such as citric, benzoic and alginic acid. Interestingly, a Phase I Randomized Safety Study investigating Acidform as a non-hormonal topical contraceptive demonstrated an increase in irritation in treated subjects, as well as a decrease in anti-inflammatory cytokine IL-1RA (Keller et al 2012, *Plos ONE* 7:e46901).

Similarly, this ability to reduce pH and thereby maintain a pH conducive to microbicidal activity is a useful adjunct to the major active components present in these gels.

In work leading up to the present invention, it has been surprisingly determined that although carboxylic acids have been shown to be anti-inflammatory in the gut and pro-inflammatory in the human reproductive tract, lactic acid functions entirely contrarily. Specifically, it has been unexpectedly found that within the human female reproductive tract, lactic acid exerts anti-inflammatory activity. Still further, it has also been determined that, in fact, carboxylic acids such as acetic acid and citric acid (which are often formulated together with lactic acid in vaginal gels), could actually antagonise the activity of lactic acid. Still further, this anti-inflammatory activity does not require the lactic acid to be used at high concentrations. Rather, use of lactic acid at physiological concentrations is anti-inflammatory.

The findings of the present invention have now facilitated the development of methods and agents directed to down-regulating inflammation in the female reproductive tract by administering lactic acid to the mucosal surface of the reproductive tract. Accordingly, there are now provided methods for both the therapeutic or prophylactic treatment of unwanted or inappropriate inflammatory responses of the female reproductive tract.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method for down-regulating inflammation in the reproductive tract or genital tissue of a female mammal said method comprising the mucosal administration of a composition comprising an organic acid having the formula (I) or in vivo hydrolysable esters or phosphate esters and salts thereof (I):

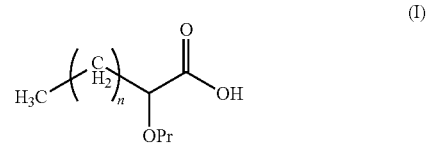

wherein n is an integer from 0 to 10;
wherein Pr is hydrogen or an in vivo hydrolysable protecting group; and
wherein the compound is in the form of a racemate, enantiomer or a mixture of enantiomers and
wherein said mucosa is contacted with an effective concentration of approximately 0.1%-1.9% of said organic acid.

In another aspect there is provided a method of down-regulating inflammation in the reproductive tract or genital tissue of a female human said method comprising the mucosal administration of a composition comprising an organic acid having the formula (I) or in vivo hydrolysable esters or phosphate esters and salts thereof:

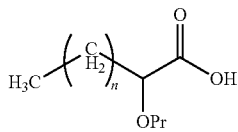

(I)

wherein n is an integer from 0 to 10;
wherein Pr is hydrogen or an in vivo hydrolysable protecting group; and
wherein the compound is in the form of a racemate, enantiomer or a mixture of enantiomers and wherein said mucosa is contacted with an effective concentration of approximately 0.1%-1.9% of said organic acid.

In still another aspect there is provided a method of down-regulating inflammation in the vagina or genital mucosa of a female human said method comprising the mucosal administration of a composition comprising and organic acid having the formula (I) or in vivo hydrolysable esters or phosphate esters and salts thereof:

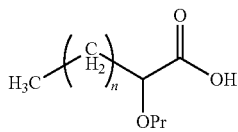

(I)

wherein n is an integer from 0 to 10;
wherein Pr is hydrogen or an in vivo hydrolysable protecting group; and
wherein the compound is in the form of a racemate, enantiomer or a mixture of enantiomers and
wherein said mucosa is contacted with an effective concentration of approximately 0.1%-1.9% of said organic acid.

In one embodiment of the organic acid of formula (I), n is an integer from 0 to 5.

In another embodiment of the organic acid of formula (I), n is 0.

In still another embodiment of the organic acid of formula (I), Pr is sulfonate, ester or carbonate.

In yet still another embodiment of the organic acid of formula (I), n is 0 and Pr is hydrogen, that is, said acid is lactic acid.

In yet another aspect of the present invention there is provided a method of down-regulating inflammation in the reproductive tract or genital tissue of a human said method comprising the mucosal administration of a composition comprising lactic acid or hydrolysable ester or phosphate ester or salt thereof and wherein said mucosa is contacted with an effective concentration of approximately 0.1%-1.9% of said organic acid.

In still another aspect there is provided a method of down-regulating inflammation in the reproductive tract or genital tissue of a female mammal said method comprising the mucosal administration of a composition comprising an organic acid having the formula (I) or in vivo hydrolysable esters or phosphate esters and salts thereof:

wherein n is an integer from 0 to 10;
wherein Pr is hydrogen or an in vivo hydrolysable protecting group; and
wherein the compound is in the form of a racemate, enantiomer or a mixture of enantiomers and
wherein said mucosa is contacted with an effective concentration of approximately 0.1%-1.9% of said organic acid; and
wherein said composition does not comprise carboxylic acids other than the organic acid of formula (I).

In one embodiment there is provided a method of down-regulating inflammation in the reproductive tract or genital tissue of a female mammal said method comprising the mucosal administration of a composition comprising an organic acid having the formula (I) or in vivo hydrolysable esters or phosphate esters and salts thereof:

(I)

wherein n is an integer from 0 to 10;
wherein Pr is hydrogen or an in vivo hydrolysable protecting group; and wherein the compound is in the form of a racemate, enantiomer or a mixture of enantiomers and wherein said mucosa is contacted with an effective concentration of approximately 0.3% -1.5% v/v of said organic acid.

In another embodiment said concentration is 0.3%-1.4%, 0.3%-1.3%, 0.3%-1.2%, 0.3%-1.1% or 0.3%-1.0% v/v.

In another embodiment, said concentration is 0.3%, 0.4%, 0.5%, 0.6%, 0.7%, 0.8%, 0.9%, 1.0%, 1.1%, 1.2%, 1.3%, 1.4%, 1.5% v/v.

In a further aspect there is provided a method of down-regulating inflammation in the reproductive tract or genital tissue of a female mammal said method comprising the mucosal administration of a composition comprising a microbicide together with an organic acid having the formula (I) or in vivo hydrolysable esters or phosphate esters and salts thereof:

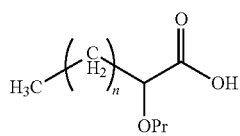

(I)

wherein n is an integer from 0 to 10;
wherein Pr is hydrogen or an in vivo hydrolysable protecting group; and
wherein the compound is in the form of a racemate, enantiomer or a mixture of enantiomers and wherein said mucosa is contacted with an effective concentration of approximately 0.1%-1.9% of said organic acid.

Another further aspect of the present invention provides a method of therapeutically or prophylactically treating a condition characterised by an aberrant, unwanted or otherwise inappropriate inflammatory response in the reproductive tract or the genital tissue of a female mammal said method comprising the mucosal administration of a composition comprising an organic acid having the formula (I) or in vivo hydrolysable esters or phosphate esters and salts thereof:

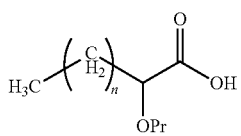

(I)

wherein n is an integer from 0 to 10;
wherein Pr is hydrogen or an in vivo hydrolysable protecting group; and
wherein the compound is in the form of a racemate, enantiomer or a mixture of enantiomers and
wherein said mucosa is contacted with an effective concentration of approximately 0.1%-1.9% of said organic acid.

In a related aspect there is provided the use of an effective amount of a composition comprising an organic acid having the formula (I) or in vivo hydrolysable esters or phosphate esters and salts thereof:

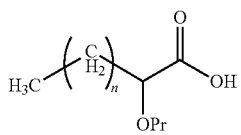

(I)

wherein n is an integer from 0 to 10;
wherein Pr is hydrogen or an in vivo hydrolysable protecting group; and
wherein the compound is in the form of a racemate, enantiomer or a mixture of enantiomers in the manufacture of a medicament for the treatment or prophylaxis of a condition characterised by an aberrant, unwanted or otherwise inappropriate inflammatory response in the reproductive tract or genital tissues of a female mammal and wherein said mucosa is contacted with an effective concentration of approximately 0.1%-1.9% of said organic acid.

In a further aspect, the present invention is directed to a pharmaceutical composition comprising an organic acid having the formula (I) or in vivo hydrolysable esters or phosphate esters and salts thereof:

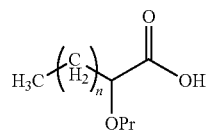

(I)

wherein n is an integer from 0 to 10;

wherein Pr is hydrogen or an in vivo hydrolysable protecting group; and
wherein the compound is in the form of a racemate, enantiomer or a mixture of enantiomers
together with one or more pharmaceutically acceptable carriers and/or diluents.

In some embodiments, according to any of the hereinbefore mentioned aspects, the organic acid may comprise a distribution of oligomers or polymers formed, for example, via intermolecular esterification.

BRIEF DESCRIPTION OF THE DRAWINGS

FIGS. 4A-B are a graphical representation depicting that L-lactic acid (0.3%, pH 3.9) abrogates IL-6 (A) and IL-8 (B) production elicited by TLR-3 agonist (Poly (I:C); PIC) on VK2, End and Ect epithelial cells *denotes p<0.05, p<0.01, *p<0.001.

FIGS. 16A-F is a graphical representation depicting the production of the anti-inflammatory cytokine IL-1RA (A), the pro-inflammatory cytokines IL-8 (B), IL-6 (C) and TNF (D) and the chemokines RANTES (E) and MIP3α (F) from Ect cells after stimulation with PIC for 1 hour in the presence of LA-containing gels, 0.3% LA alone or low pH 3.9 (HCl). Mean and SD are shown from 2 independent experiments.

DETAILED DESCRIPTION OF THE INVENTION

Figure 1:
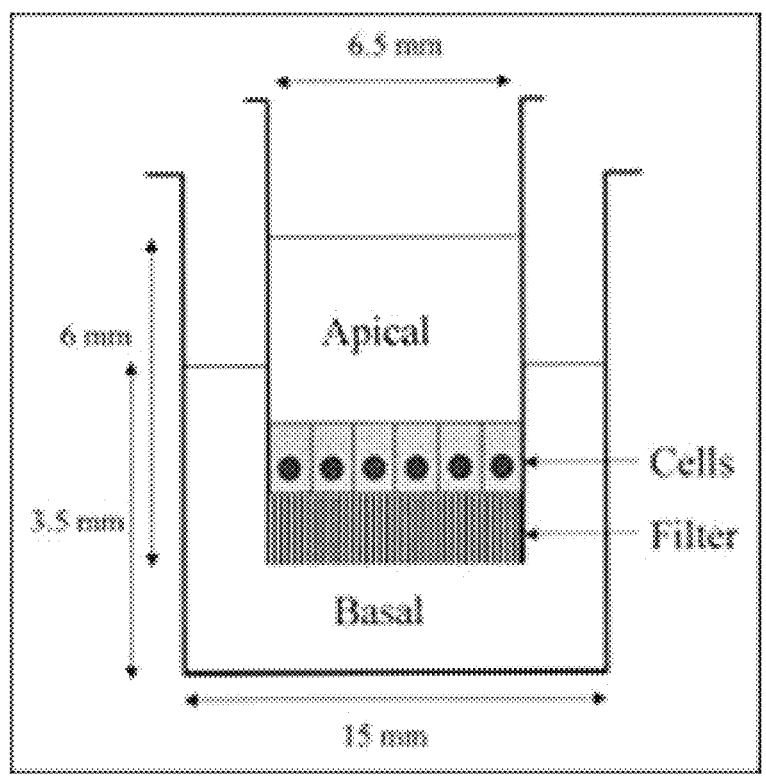
FIG. 1 is a diagrammatic representation of a transwell culture system. Acid is added to the apical chamber.

The present invention is predicated, in part, on the unexpected determination that lactic acid functions as an anti-inflammatory agent within the female reproductive tract. Specifically, whereas carboxylic acids, generally, have been found to function as anti-inflammatories in the gut, they function in a pro-inflammatory manner in the unique microenvironment of the reproductive tract. Lactic acid, however, although having been shown by Mossop et al to be pro-inflammatory in the reproductive tract, has now been determined to function in an anti-inflammatory manner in the female reproductive tract. Still further, the functional activity of lactic acid is, in fact, antagonised by other carboxylic acids such as acetic acid, tartaric acid and alginic acid. Accordingly, the physiological and immunological functioning of lactic acid in the context of the reproductive tract is counter-intuitive, particularly when considered in light of the fact that even concentrations of lactic acid much higher than physiological levels have been assumed to be either relatively inert when administered to the female reproductive tract or to do no more than provide pH buffering or acidification effects. Lactic acid has therefore been regularly used as an excipient in vaginal gels. In fact, may be likely that the lack of any significant functionality of lactic acid in this context is due to the antagonistic activity of other carboxylic acids, present in these formulations, on lactic acid. Accordingly, these findings have now facilitated the rational design of means for down-regulating an inflammatory response in the female reproductive tract and genital tissue. There is therefore also now provided a means for therapeutically or prophylactically treating conditions, such as vaginitis, which are characterised by inflammation.

Accordingly, one aspect of the present invention is directed to a method for down-regulating inflammation in the reproductive tract or genital tissue of a female mammal said method comprising the mucosal administration of a composition comprising an organic acid having the formula (I) or in vivo hydrolysable esters or phosphate esters and salts thereof:

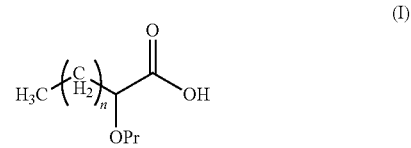

(I)

wherein n is an integer from 0 to 10;
wherein Pr is hydrogen or an in vivo hydrolysable protecting group; and
wherein the compound is in the form of a racemate, enantiomer or a mixture of enantiomers and
wherein said mucosa is contacted with an effective concentration of approximately 0.1% -1.9% v/v of said organic acid.

The term "mammal" as used herein includes humans, primates, livestock animals (eg. horses, cattle, sheep, pigs, donkeys), laboratory test animals (eg. mice, rats, guinea pigs), companion animals (eg. dogs, cats) and captive wild animals (eg. kangaroos, deer, foxes). As detailed hereinbefore, the female reproductive tract of human females is particularly unusual since it is a significantly more acidic microenvironment than the female reproductive tract of other non-human primates. The exceptional and unique physiology of the human female reproductive tract is consistent with the fact that most carboxylic acids have been found to exhibit pro-inflammatory activity in the human reproductive tract despite exhibiting anti-inflammatory activity in other tissue microenvironments, such as the gut. In the context of lactic acid, however, which is also a carboxylic acid, it has been determined that it exhibit anti-inflammatory activity in the reproductive tract. Accordingly, in one embodiment, said mammal is a human.

According to this embodiment there is provided a method of down-regulating inflammation in the reproductive tract or genital tissue of a female human said method comprising the mucosal administration of a composition comprising an organic acid having the formula (I) or in vivo hydrolysable esters or phosphate esters and salts thereof:

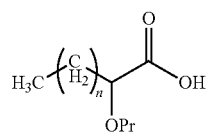

(I)

wherein n is an integer from 0 to 10;
wherein Pr is hydrogen or an in vivo hydrolysable protecting group; and
wherein the compound is in the form of a racemate, enantiomer or a mixture of enantiomers and wherein said mucosa is contacted with an effective concentration of approximately 0.1% -1.9% v/v of said organic acid.

Reference to "reproductive tract" of a female mammal should be understood as a reference to the organs and tissues which contribute towards the reproductive process. Without limiting the present invention to any one theory or mode of action, the female reproductive tract comprises three main parts: the vagina, the uterus, and the ovaries. The vagina meets the external environment at the vulva, which also includes the labia, clitoris and urethra. The vagina is attached to the uterus through the cervix, while the uterus is attached to the ovaries via the fallopian tubes. Reference to "reproductive tract" should therefore be understood as a reference to all or part of any one or more of these organs or tissues. Reference to the "genital tissue" should be understood as a reference to all of the external female genitalia including but not limited to the labium majora, labium minora, clitoris, perineum, vulva and urethral orifice. In one embodiment, said reproductive tract is the vagina and said genital tissue is genital mucosa.

Without limiting the present invention to any one theory or mode of action the mucous membranes are linings of mostly endodermal origin, covered in epithelium, which are involved in absorption and secretion. They line cavities that are exposed to the external environment and internal organs, in particular the vagina and genitalia. They are at several places contiguous with skin, such as the genital area, and the anus.

According to this embodiment there is provided a method of down-regulating inflammation in the vagina or genital mucosa of a female human said method comprising the mucosal administration of a composition comprising and organic acid having the formula (I) or in vivo hydrolysable esters or phosphate esters and salts thereof:

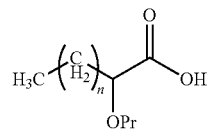

(I)

wherein n is an integer from 0 to 10;
wherein Pr is hydrogen or an in vivo hydrolysable protecting group; and
wherein the compound is in the form of a racemate, enantiomer or a mixture of enantiomers and
wherein said mucosa is contacted with an effective concentration of approximately 0.1% -1.9% v/v of said organic acid.

Still without limiting the present invention to any one theory or mode of action, the inflammatory response is a complex response characterised by a series of physiological and/or immunological events which are induced to occur by the release of a cytokine cascade in response to any one of a variety of stimuli including, but not limited to, tissue injury, infection, an immune response (such as to a pathogen or an innocuous agent—as occurs with allergies) or disease (such as tumour formation or an autoimmune response).

The physiological events which characterise inflammation include:
(i) vasodilation
(ii) increased vascular permeability
(iii) cellular infiltration
(iv) changes to the biosynthetic, metabolic and catabolic profiles of affected organs
(v) activation of the cells of the immune system.

It should be understood that reference to "inflammation" or an "inflammatory response" is a reference to any one or more of the physiological and/or immunological events or phases that are induced to occur in the context of inflammation and, specifically, in response to the signals generated by the cytokine cascade which directs the inflammatory response. For example IL-1, TNFα and IL-6 are well known for their functions as pro-inflammatory mediators. It should also be understood that an inflammatory response within the context of the present invention includes a reference to a partial response, such as a response which has only just commenced, or to any specific phase or event of a response (such as the phases and events detailed in points (i)-(v), above, or any other effect related to inflammation). Further, it should also be understood that depending on any given set of specific circumstances, the end point of an inflammatory response may vary. For example, in some situations there may only occur an acute vascular response. To the extent that "acute" inflammation occurs, this is generally understood to include the events of both an acute vascular response and an acute cellular response. Some inflammatory responses will resolve at the acute stage while others may progress to become chronic cellular responses.

In certain circumstances the acute process, characterized by neutrophil infiltration and oedema, gives way to a predominance of mononuclear phagocytes and lymphocytes. This is thought to occur to some degree with the normal healing process but becomes exaggerated and chronic when there is ineffective elimination of foreign materials as in certain infections or following introduction of foreign bodies or deposition of crystals (e.g. urate crystals). Chronic inflammation is often associated with fusion of mononuclear cells to form multinucleated gigant cells, which eventually become a granuloma. Chronic inflammation is also seen under conditions of delayed hypersensitivity.

Examples of inflammatory responses include, but are not limited to vaginitis (induced by, for example, irritants, infectious agents such as pathogens, imbalance of commensal bacteria, allergy or hormones), vaginosis tissue injury, diabetes and semen. In another example, the inflammatory response may also be a side effect resulting from a course of treatment directed to an unrelated condition. For example, tenofovir is known to decrease the functionality of some anti-inflammatory mediators. Accordingly, inflammation which is the subject of treatment in accordance with the method of the invention is not limited in terms of how it has been caused. Without limiting the present invention to any one theory or mode of action, vaginitis is an inflammation of the vagina. It can result in discharge, itching and pain, and is often associated with an irritation or infection of the vulva. It is usually caused due to infection. The three main kinds of infectious vaginitis are bacterial vaginosis, vaginal candidiasis, and trichomoniasis. A woman may have any combination of vaginal infections at one time.

Infectious vaginitis accounts for 90% of all cases in reproductive age women. Other less common infections are caused by gonorrhea, *chlamydia, Mycoplasma*, herpes, HIV, *Campylobacter*, improper hygiene, and some parasites, notably *Trichomonas vaginalis*.

Vaginal infections are often a mix of various etiologies, which can present challenging cases for treatment. Indeed, when only one cause is treated, the other pathogens can gain in resistance and induce relapses and recurrences. Further, either a change in pH balance or introduction of foreign bacteria in the vagina can also lead to infection. To this end, there are physical factors that can contribute to the development of infection, such as a constant wet vulva due to tight clothing, chemicals contacting the vagina via scented tampons, antibiotics, birth control pills/injections, douching, or a diet favouring refined sugar and yeast.

Hormonal vaginitis includes atrophic vaginitis usually found in postmenopausal or postpartum women. Sometimes it can occur in young girls before puberty. In these situations the estrogen support of the vagina is poor.

Irritant vaginitis can be caused by allergies to condoms, spermicides, soaps, perfumes, douches, lubricants and semen. It can also be caused by hot tubs, abrasion, tissue, tampons or topical medications. Foreign bodies (most commonly retained tampons or condoms) can also cause extremely malodorous vaginal discharges.

It should be understood that the inflammation which is treated by the method of the present invention may be the result of any cause. In one embodiment, said inflammation is infectious vaginitis.

Without limiting the present invention to any one theory or mode of action lactic acid is a carboxylic acid with the chemical formula $C_3H_6O_3$. It has a hydroxyl group adjacent to the carboxyl group, making it an alpha hydroxy acid. In solution, it can lose a proton from the carboxyl group, producing the lactate ion $CH_3CH(OH)COO^-$. Lactic acid is miscible with water or ethanol, and is hygroscopic. It is chiral and consists of two optical isomers. One is known as L-(+)-lactic acid or (S)-lactic acid and the other, its mirror image, is D-(−)-lactic acid or (R)-lactic acid.

In animals, L-lactate is constantly produced from pyruvate via the enzyme lactate dehydrogenase (LDH) in a process of fermentation during normal metabolism and exercise. However, it is also produced by lactic acid bacteria. The lactic acid bacteria (LAB) comprise a clade of Gram-positive, low-GC, acid-tolerant, generally non-sporulating, non-respiring rod or cocci that are associated by their common metabolic and physiological characteristics. These bacteria produce lactic acid as the major metabolic end-produce of carbohydrate fermentation. LAB contribute to the healthy microflora of human mucosal surfaces. The genera that comprise the LAB are at its core *Lactobacillus, Leuconostoc, Pediococcus, Lactococcus*, and *Streptococcus* as well as the more peripheral *Aerococcus, Carnobacterium, Enterococcus, Oenococcus, Sporolactobacillus, Tetragenococcus, Vagococcus*, and *Weisella*; these belonging to the order Lactobacillales.

The method of the present invention is predicated on the administration to the mucosa of the reproductive tract or the genital tissue of an organic acid having the formula (I) or in vivo hydrolysable esters or phosphate esters and salts thereof:

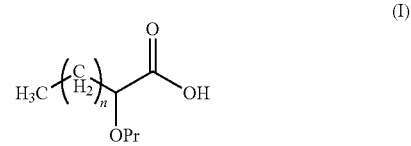

wherein n is an integer from 0 to 10;
wherein Pr is hydrogen or an in vivo hydrolysable protecting group; and
wherein the compound is in the form of a racemate, enantiomer or a mixture of enantiomers.

The term "pharmaceutically acceptable salt" should be understood to refer to salts which retain their biological effectiveness and properties of the disclosed compounds and which are not biologically or otherwise undesirable. Suitable salts include those derived from alkali metals such as potassium and sodium, alkaline earth metals such as calcium and magnesium, and ammonium salts.

Preferred in vivo hydrolysable esters or phosphate esters are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the omega-(amino, mono- or di-lower alkylamino, carboxy, lower alkoxycarbonyl)-lower alkyl esters, the alpha-(lower alkanoyloxy, lower alkoxycarbonyl or di-lower alkylaminocarbonyl)-lower alkyl esters, phosphate esters and the like conventionally used in the art.

A wide variety of protecting groups suitable for protecting the hydroxyl group I the compound of formula (I) are well-known in the art. For example, the hydroxyl functional group may be protected as a sulfonate, ester or carbonate promoiety, which may be hydrolyzed in vivo to provide the hydroxyl group.

In one embodiment of the organic acid of formula (I), n is an integer from 0 to 5.

In another embodiment of the organic acid of formula (I), n is 0.

In still another embodiment of the organic acid of formula (I), Pr is sulfonate, ester or carbonate.

In yet still another embodiment of the organic acid of formula (I), n is 0 and Pr is hydrogen, that is, said acid is lactic acid.

Accordingly, in one preferred aspect of the present invention there is provided a method of down-regulating inflammation in the reproductive tract or genital tissue of a human said method comprising the mucosal administration of a composition comprising lactic acid or hydrolysable ester or phosphate ester or salt thereof and wherein said mucosa is contacted with an effective concentration of approximately 0.1%-1.9% v/v of said lactic acid.

In another embodiment said reproductive tract is the vagina and said genital tissue is genital mucosa.

Reference to "down-regulating" an inflammatory response should be understood as a reference to preventing, reducing (eg. slowing) or otherwise inhibiting one or more aspects of an inflammatory response.

The present invention is predicated on the localised delivery of lactic acid to the mucosal tissue of the reproductive tract and/or the genitals. Reference to "mucosal administration" should therefore be understood as a reference to introducing the subject composition to the mammal by any route which will enable it to contact the mucosal immune tissue of the genital or reproductive tract. Typically, this can be achieved by administering the composition via an intravaginal route such as via topically applied compositions or locally administered injections. Although said mucosal administration will generally take the form of administration directly to mucosal tissue, the present invention nevertheless extends to other modes of administration which nevertheless may achieve delivery of lactic acid to the vaginal or genital mucosa.

Although it has been determined that lactic acid functions as an anti-inflammatory molecule in the reproductive tract of the human female, in a further aspect it has still further been surprisingly determined that lactic acid anti-inflammatory functionality is antagonised by the presence of other acids, in particular other organic or carboxylic acids such as acetic acid, citric acid, tartaric acid and alginic acid. Most microbicidal and feminine hygiene products are formulated with both lactic acid as an excipient and other carboxylic acids which function to lower the pH of the vagina. Although lactic acid is not designed to function as an active ingredient in these formulations, it is now known that the fact that it is assumed to be relatively inert (even at the high concentrations at which it is used—>4% v/v), the presence of other carboxylic acids would have nevertheless antagonised the previously unrecognised anti-inflammatory properties of lactic acid, thereby effectively rendering said lactic acid inert and therefore useful to be used as a mere excipient. However, in light of the findings of the present invention, it has now been demonstrated that lactic acid will produce a particularly effective anti-inflammatory response when it is formulated without other carboxylic acids.

According to this related aspect there is provided a method of down-regulating inflammation in the reproductive tract or genital tissue of a female mammal said method comprising the mucosal administration of a composition comprising an organic acid having the formula (I) or in vivo hydrolysable esters or phosphate esters and salts thereof:

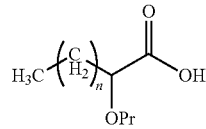

(I)

wherein n is an integer from 0 to 10;
wherein Pr is hydrogen or an in vivo hydrolysable protecting group; and
wherein the compound is in the form of a racemate, enantiomer or a mixture of enantiomers and wherein said mucosa is contacted with an effective concentration of approximately 0.1% -1.9% v/v of said organic acid; and
wherein said composition does not comprise carboxylic acids other than the organic acid of formula (I).

As detailed hereinbefore it has been determined that the anti-inflammatory properties of lactic acid are functional when lactic acid is used at physiological levels. This finding is unexpected when considered in light of the fact that lactic acid is currently used as an inert excipient at concentrations well above physiological levels. Without limiting the present invention to any one theory or mode of action, lactic acid is generally found in the lower human female reproductive tract at a concentration of approximately 1% v/v. To this end, lactic acid has now been determined to exhibit anti-inflammatory functionality when used at a concentration of as low as 0.1% up to about 1.9% v/v, preferably 0.2%-1.8%, 0.3%-1.7%, 0.3%-1.6%, 0.3%-1.5%, 0.3%-1.4%, 0.3%-1.3%, 0.3%-1.2%, 0.3%-1.1% or 0.3%-1% v/v.

In this regard, reference to the "contacting" the mucosa with an "effective concentration" of approximately 0.1%-1.9% v/v should be understood to mean that the concentrations of the subject organic acid which acts on the vaginal mucosal tissue is at this concentration. It would be appreciated by the person of skill in the art that the concentrations of the organic acid as formulated in the product which is provided to a patient to use may be at a higher concentration. This may be due to the inherent dilution or dissipation loss of active ingredient which occurs subsequently to application of the product but prior to it functionally acting on the mucosa. For example, an oral formulation may have to be formulated at a high concentration to allow for dissipation of the active ingredient as it is processed through the digestive system. In another example, in the context of a topical formulation the concentration of the active ingredient in the gel or cream itself may have to be adjusted to take into account the relative viscosity of the gel or cream and therefore the extent to which it is likely to become diluted by the natural vaginal fluids. That is, it may be necessary to prepare a topical formulation at a higher concentration such that any dilution which may inherently occur subsequently to its application leads to an effective concentration of 0.1%-1.9% v/v being delivered to the mucosal tissue. It is well within the skill of the person in the art to calculate and generate an appropriate formulation.

In one embodiment there is provided a method of down-regulating inflammation in the reproductive tract or genital tissue of a female mammal said method comprising the mucosal administration of a composition comprising an organic acid having the formula (I) or in vivo hydrolysable esters or phosphate esters and salts thereof:

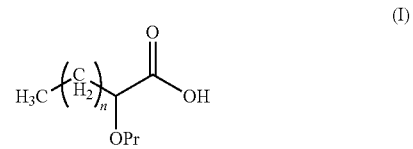

(I)

wherein n is an integer from 0 to 10;
wherein Pr is hydrogen or an in vivo hydrolysable protecting group; and wherein the compound is in the form of a racemate, enantiomer or a mixture of enantiomers and
wherein said mucosa is contacted with an effective concentration of approximately 0.3%-1.5% v/v of said organic acid.

In another embodiment said concentration is 0.3%-1.4%, 0.3%-1.3%, 0.3% -1.2%, 0.3%-1.1% or 0.3%-1.0% v/v.

In another embodiment, said concentration is 0.3%, 0.4%, 0.5%, 0.6%, 0.7%, 0.8%, 0.9%, 1.0%, 1.1%, 1.2%, 1.3%, 1.4%, 1.5% v/v.

It would be understood by the person of skill in the art that reference to the above percentage values are approximate to the extent that some deviation from these specific percentages is acceptable and provides a functionally equivalent proportion. It is well within the skill of the person in the art to determine, based on very simple and routine in vitro or in vivo testing systems, to what extent some deviation from these percentage values is enabled. For example, it is to be expected that from about 0.1%-1.5% v/v lactic acid will be effective, in particular 0.5%-1.5%, 0.8%-1.2%, 0.9%-1.1% or 0.1%, 0.2%, 0.3%, 0.4%, 0.5%, 0.6%, 0.7%, 0.8%, 0.9%, 1.0%, 1.1%, 1.2%, 1.3%, 1.4% or 1.5%.

In a further related aspect of the present invention it has been determined that the anti-inflammatory properties of lactic acid are functional when lactic acid is used at physiologically relevant pH levels. Without limiting the present invention to any one theory or more of action, lactic acid is generally found in the lower human female reproductive tract at a pH of 3.5. To this end, lactic acid has now been determined to exhibit anti-inflammatory functionality when used at a pH level of as low as pH 2.8 up to about pH 4.2, preferably pH 3.2-3.8.

In accordance with these aspects of the invention, in one embodiment said female mammal is a human.

In another embodiment, said reproductive tract is the vagina and said genital tissue is the genital mucosa.

In yet another embodiment, n is an integer from 0 to 5.

In still another embodiment n is 0.

In yet still another embodiment, n is 0 and Pr is hydrogen.

In a further embodiment, said organic acid is lactic acid.

In yet a another related aspect of the present invention there is provided a method of down-regulating the inflammation in the reproductive tract or genital tissue of a female mammal said method comprising the mucosal administration of a composition comprising lactic acid wherein said mucosa is contacted with an effective concentration of 0.3%-1.5% v/v of said lactic acid.

In another embodiment said concentration is 0.3%-1.4%, 0.3%-1.3%, 0.3% -1.2%, 0.3%-1.1% or 0.3%-1.0% v/v.

In another embodiment, said concentration is 0.3%, 0.4%, 0.5%, 0.6%, 0.7%, 0.8%, 0.9%, 1.0%, 1.1%, 1.2%, 1.3%, 1.4%, 1.5% v/v. In accordance with the method of the present invention, the composition defined herein may be coadministered with one or more other compounds or molecules. By "coadministered" is meant simultaneous administration in the same formulation or in two different formulations via the same or different routes or sequential administration by the same or different routes. For example, the subject agent may be administered together with an agonistic agent in order to enhance its effect or with another active ingredient selected to treat a symptom or cause of said inflammation. By "sequential" administration is meant a time difference of from second, minutes, hours or days between the administration of the two types of molecules. These molecules may be administered in any order.

In one embodiment, the composition of the present invention may be formulated together with a one or more ingredients designed to sooth or otherwise provide immediate relief from the symptoms associated with vaginal or genital inflammation, such as those associated with vaginitis or vaginosis, these symptoms including:

irritation and/or itching of the genital area;
inflammation (irritation, redness, and swelling caused by the presence of extra immune cells) of the labia majora, labia minora, or perineal area;
vaginal discharge;
foul vaginal odour;
pain/irritation with sexual intercourse.

In another embodiment, and to the extent that the composition of the present invention is designed to prophylactically or therapeutically treat pathogen-induced vaginitis or vaginosis, one may seek to formulate the composition together with a microbicide.

Without limiting the present invention to any one theory or mode of action, a microbicide is a compound or substance which reduces the infectivity of a pathogen, such as a bacterium, virus, parasite, fungus or the like. Examples of microbicides which one may seek to use include, but are not limited to:

antibiotics
bactericides
disinfectants
fungicides
detergents (eg. nonoxynol-9, SAVVY)
pH modifiers (eg. buffer gel)
antiretroviral based microbicides (eg. tenofovir based microbicide, integrase inhibitors, reverse transcriptase inhibitors (such as PMPA, VC-781, TMC120, MIV 150), entry inhibitors (including but not limited to CCR5, CXCR4 antagonists, antibodies to CD4, dendrimer, carbohydrates (Griffithsin)), HIV protease inhibitors, Cyanovirin, HIV neutralizing Abs. linear polyanions (e.g. Carraguard, dextran sulphate, PRO2000).

According to this embodiment, there is therefore provided a method of down-regulating inflammation in the reproductive tract or genital tissue of a female mammal said method comprising the mucosal administration of a composition comprising a microbicide together with an organic acid having the formula (I) or in vivo hydrolysable esters or phosphate esters and salts thereof:

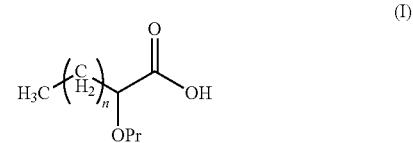

(I)

wherein n is an integer from 0 to 10;
wherein Pr is hydrogen or an in vivo hydrolysable protecting group; and
wherein the compound is in the form of a racemate, enantiomer or a mixture of enantiomers and
wherein said mucosa is contacted with an effective concentration of approximately 0.1% -1.9% v/v of said organic acid.

In accordance with this embodiment said female mammal is preferably a human.

In another embodiment, said reproductive tract is the vagina and said genital tissue is the genital mucosa.

In yet another embodiment, n is an integer from 0 to 5.

In still another embodiment n is 0.

In yet still another embodiment, n is 0 and Pr is hydrogen.

In a further embodiment, said organic acid is lactic acid.

In a still further embodiment, said composition does not comprise carboxylic acids other than the organic acid of formula (I).

In yet still another embodiment, said composition comprises a concentration of 0.1%-1.9%, preferably 0.2%-1.8%, 0.3%-1.5%, 0.3%-1.6%, 0.3%-1.5%, 0.3%-1.4%; 0.3%-1.3%, 0.3%-1.2%, 0.3%-1.1% or 0.3%-1.0% v/v of the organic acid of formula (I).

As detailed hereinbefore, a further aspect of the present invention relates to the use of the invention in relation to the treatment and/or prophylaxis of disease conditions or other unwanted conditions which are characterised by an inflammatory response.

The present invention therefore contemplates a method of therapeutically or prophylactically treating a condition characterised by an aberrant, unwanted or otherwise inappropriate inflammatory response in the reproductive tract or the genital tissue of a female mammal said method comprising the mucosal administration of a composition comprising an organic acid having the formula (I) or in vivo hydrolysable esters or phosphate esters and salts thereof:

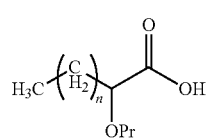

(I)

wherein n is an integer from 0 to 10;
wherein Pr is hydrogen or an in vivo hydrolysable protecting group; and
wherein the compound is in the form of a racemate, enantiomer or a mixture of enantiomers and
wherein said mucosa is contacted with an effective concentration of approximately 0.1%-1.9% v/v of said organic acid.

In a related aspect there is provided the use of a composition comprising an organic acid having the formula (I) or in vivo hydrolysable esters or phosphate esters and salts thereof:

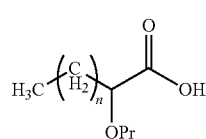

(I)

wherein n is an integer from 0 to 10;
wherein Pr is hydrogen or an in vivo hydrolysable protecting group; and
wherein the compound is in the form of a racemate, enantiomer or a mixture of enantiomers in the manufacture of a medicament for the treatment or prophylaxis of a condition characterised by an aberrant, unwanted or otherwise inappropriate inflammatory response in the reproductive tract or genital tissues of a female mammal and wherein said mucosa is contacted with an effective concentration of approximately 0.1% -1.9% v/v of said organic acid.

Reference to an "aberrant, unwanted or otherwise inappropriate" inflammatory response should be understood as a reference to an excessive response, an inadequate response or to a physiologically normal response which is inappropriate in that it is unwanted or otherwise inappropriate. Examples of aberrant or otherwise unwanted inflammatory responses include those which occur in the context of infectious vaginitis, atrophic vaginitis, irritant vaginitis, pelvic inflammatory disease or traumatic injury, such as occurs with surgery. In this regard, however, some forms of inflammation associated with irritant vaginitis in fact reflect normal physiological responses which are unwanted, such as those which occur in the context of an allergy.

In one embodiment, said condition is infectious vaginitis, vaginosis, atrophic vaginitis, irritant vaginitis or traumatic injury.

In another embodiment, said condition is caused by a pathogen.

Reference to "infection" should be understood as a reference to the detrimental or otherwise unwanted colonisation of the reproductive tract of a female mammal by a pathogen. To this end, the subject infection may occur in any one or more regions, or parts, of the reproductive tract (such as in the context of one or more tissue regions). It may also be an infection which, although being evident in all or part of the reproductive tract, is also found in non-reproductive tract tissues, regions or organs of the mammal. For example, although HIV infection can be introduced via the reproductive tract tissue it is ultimately an infection which spreads systemically. Still further reference to an infection "of" the reproductive tract should be understood to encompass an infection which is only transiently present in the reproductive tract, such as an infection which enters the body by this route but ultimately localises elsewhere.

In accordance with these aspects of the invention, said female mammal is preferably a human.

In another embodiment, said reproductive tract is the vagina and said genital tissue is the genital mucosa.

In yet another embodiment, n is an integer from 0 to 5.
In still another embodiment n is 0.
In yet still another embodiment, n is 0 and Pr is hydrogen.
In a further embodiment, said organic acid is lactic acid.
In a still further embodiment, said composition does not comprise carboxylic acids other than the organic acid of formula (I).

In yet still another embodiment, said composition comprises a concentration of 0.1%-1.9%, preferably 0.2%-1.8%, 0.3%-1.5%, 0.3%-1.6%, 0.3%-1.5%, 0.3%-1.4%, 0.3%-1.3%, 0.3%-1.2%, 0.3%-1.1% or 0.3%-1.0% v/v of the organic acid of formula (I).

In another embodiment said concentration is 0.3%-1.4%, 0.3%-1.3%, 0.3% -1.2%, 0.3%-1.1% or 0.3%-1.0% v/v.

In another embodiment, said concentration is 0.3%, 0.4%, 0.5%, 0.6%, 0.7%, 0.8%, 0.9%, 1.0%, 1.1%, 1.2%, 1.3%, 1.4%, 1.5% v/v.

In still yet another embodiment, said composition is formulated together with a microbicide.

It would be appreciated by the person of skill in the art that in formulating the composition of the present invention, surfactants may be added to the subject compositions. The surfactants may provide for better surface contact of the compositions with the vaginal mucosa by further reducing surface tension and promoting dispersal of the active substances. Surfactants that may be added include but are not limited to lauryl sulfate and teepol, and the like.

The pharmaceutical compositions of this invention may further comprise other additives such as gelling agents, buffers, preservatives, detergents, oils, alcohols, emulsifiers, solubilisers, humectants, and bioadhesives.

The pharmaceutical compositions of this invention further comprise a pharmaceutically acceptable carrier suitable for vaginal and/or vulvar drug administration.

The compositions of the present invention may include a physiologically tolerable preservative. Suitable physiologically tolerable preservatives include bacteriostats, preservatives, inhibitors, and the like, such as methyl, ethyl, propyl, and butyl esters of parahydroxybenzoic acid (paraben); propyl gallate; sorbic acid and its sodium and potassium salts; propionic acid and its calcium and sodium salts; 6-acetoxy-2,4-dimethyl-m-dioxane; 2-bromo-2-nitropropane-1,3-diol; salicylanilides such as dibromosalicylanilide and tribromosalicylamilide, and cis isomer of 1-(3-chloro-allyl-3,5,7-triaza-1-azanidadamantane chloride; hexachlorophene; sodium benzoate; phenolic compounds such as butyl hydroxyanisole, butyl hydroxytoluene, chloro- and bromocresols, and chloro- and bromo-oxylenols; quaternary ammonium compound such as benzalkonium chloride; aromatic alcohols such as 2-phenylethyl alcohol and benzyl alcohol; chlorobutanol; quinoline derivatives such as iodochlorohydroxyquinoline; and the like. Preferably, the preservative is included in an amount in the range of about 0.05 to about 0.2 weight percent, on a total composition weight basis.

Pharmaceutically acceptable excipients that can be included in the pharmaceutical compositions of the present invention include, for example, physiologically tolerable surfactants, solvents, emollients, colorants, fragrances, and the like, which are well known in the art.

The compositions of the invention are applied topically or otherwise locally to the vagina and/or genital mucosa of a patient. Other examples of local administration would include local injection.

The pharmaceutical compositions may be applied in the form of a suppository, an ointment, cream, solid (eg. tablet, capsule, ovule, and suppository), solution, suspension, gel, foam, film, or liposomal composition. The composition may also be delivered as a flushable tissue used to clean the urogenital and anal mucosa. Ointments and creams, may, for example, be formulated with an aqueous or oily base with the addition of suitable thickening and/or gelling agents. One technique for applying the compositions of the claimed invention is to employ a single use packet (such as a small envelope-like structure or the like) containing an intended single unit dose. The packet is initially sealed, but is opened at the time of use by tearing, cutting, or the like at a desired or planned location in the packet after which the contents are directly administrable as labeled.

The pharmaceutical compositions may also be contained within a vaginal ring, tampon, suppository, sponge, pillow, puff, or osmotic pump system.

The dosage forms of the compositions may also be formulated in a sustained-release form, employing various polymers, fibers, resins, waxes, oils, or other pharmaceutical excipients used by those skilled in the art of medicinal chemistry to produce a prolonged release of the active constituents of the compositions.

The total daily dose of the compositions of this invention administered to a human or lower animal may range from about 100 mg to about 15 g/day. More preferable doses can be in the range of from about 500 mg to about 5 g/day. If desired the effective daily dose can be divided into multiple doses for purposes of administration; consequently, single dose compositions may contain such amounts or submultiples thereof to make up the daily dose.

The pharmaceutical forms suitable for injectable use include sterile aqueous solutions (where water soluble) or dispersions and sterile powders for the extemporaneous preparation of sterile injectable solutions or dispersion. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

In a related aspect the present invention should be understood to extend to the formulation and administration of lactic acid producing bacteria rather than the lactic acid itself. This is a commonly used approach in the context of repopulating the flora of the gut. Without limiting the present invention to any one theory or mode of action, the genus *Lactobacillus* currently consists of over 180 species. The genus is polyphyletic, with the genus *Pedeiococcus* dividing the *L. casei* group, and the species *L. acidophilus, L. salivarius,* and *L. reuteri* being representatives of three distinct subclades. The genus *Paralactobacillus* falls within the *L. salivarius* group. In recent years, other members of the genus *Lactobacillus* (formerly known as the *Leuconostoc* branch of *Lactobacillus*) have been reclassified into the genera *Atopobium, Carnobacterium, Weissella, Oenococcus,* and *Leuconostoc*. More recently, the *Pediococcus* species *P. dextrinicus* has been reclassified as a *Lactobacillus* species. The person of skill in the art would appreciate that one can select for use any suitable species which produces lactic acid. Means for preparing and administering *Lactobacillus* are known and could be adopted for administration to the reproductive tract.

The present invention also relates to an article of manufacture comprising packaging material and a composition of the invention within the packaging material. The composition is present in an amount sufficient to treat vaginal inflammation in a patient, preferably in an amount equivalent to at least one unit does. The packaging material comprises a label that indicates that the composition can be used for treating vaginal inflammation. Preferably, the label includes other printed indicia such as a listing of ingredients, the manufacturer's name and address, and the like. Preferably, the packaging material also includes a printed insert including detailed information on the composition, its method of administration for treatment of pathogenic vaginal biofilms, for example, and vaginal infections, side effects, contraindications, and the like indicia, which may be required by governmental agencies responsible for regulation of pharmaceutical products.

In a further aspect, the present invention is directed to a pharmaceutical composition comprising an organic acid having the formula (I) or in vivo hydrolysable esters or phosphate esters and salts thereof:

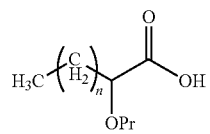

(I)

wherein n is an integer from 0 to 10;
wherein Pr is hydrogen or an in vivo hydrolysable protecting group; and
wherein the compound is in the form of a racemate, enantiomer or a mixture of enantiomers
together with one or more pharmaceutically acceptable carriers and/or diluents.

In one embodiment, n is an integer from 0 to 5.
In still another embodiment, n is 0.
In yet still another embodiment n is 0 and Pr is hydrogen.
In a further embodiment, said organic acid is lactic acid.
In a still further embodiment, said composition does not comprise carboxylic acids other than the organic acid of formula (I).

In yet still another embodiment, said composition comprises a concentration of 0.1%-1.9%, preferably 0.2%-1.8%, 0.3%-1.7%, 0.3%-1.6%, 0.3%-1.5%, 0.3%-1.4%, 0.3%-1.3%, 0.3%-1.2%, 0.3%-1.1% or 0.3%-1.0% v/v of the organic acid of formula (I).

In another embodiment said concentration is 0.3%-1.4%, 0.3%-1.3%, 0.3% -1.2%, 0.3%-1.1% or 0.3%-1.0% v/v.

In another embodiment, said concentration is 0.3%, 0.4%, 0.5%, 0.6%, 0.7%, 0.8%, 0.9%, 1.0%, 1.1%, 1.2%, 1.3%, 1.4%, 1.5% v/v.

The present invention is further defined by reference to the following non-limiting examples.

EXAMPLES

Definitions:
PIC—polyinosinic acid: cytidylic acid, poly (I:C)=viral TLR3 agonist
VK2—human epithelial cell lines from the vagina
Ect—human epithelial cell lines from the ectocervix
End—human epithelial cell lines from the endocervix
L-LA—L-enantiomer lactic acid
D-LA—D-enantiomer lactic acid
TLR—Toll-like Receptor
IL-#—Interleukin #
IL-1RA—Interleukin-1 receptor antagonist
HCl—Hydrochloric acid
FRT—female reproductive tract
TNF—Tumour necrosis factor
RANTES—regulates on activation, normal T cell expressed and secreted
MIP3α—Macrophage inflammatory protein 3 alpha Example 1

A transwell culture system (FIG. 1) has been developed, which enables epithelial cells from the lower female reproductive tract to be incubated with concentrations of L-lactic acid approaching those found in the FRT in vivo without significant toxicity, allowing the direct impact of L-lactic acid and other acids to be evaluated in an in vitro model. Human epithelial cell lines from the vagina (VK2), ectocervix (Ect) and endocervix (End) originally generated by {Fichorova, 1997} and purchased from ATCC.

Figure 2A:
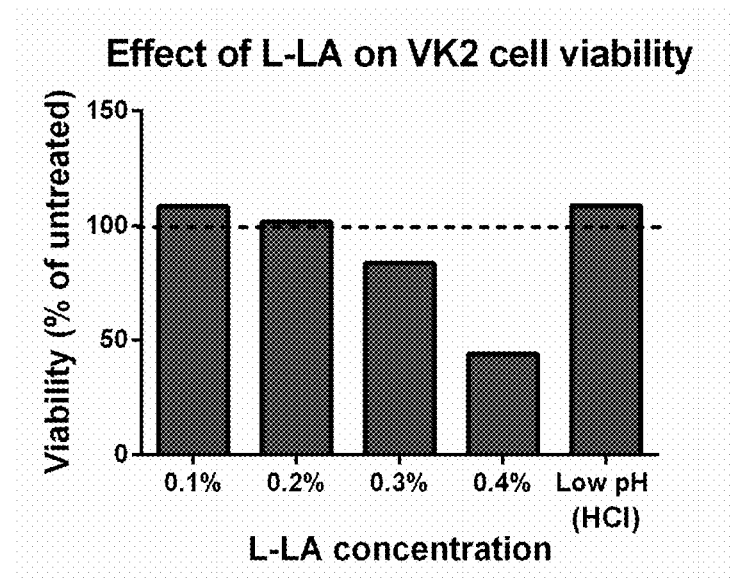
FIG. 2A shows epithelial cells were cultured in transwells for 24 hr in the presence of increasing concentrations of L-lactic acid added to the upper chamber. Cell viability was assessed via MTS.

These cells tolerated L-lactic acid concentrations up to 0.4% when added to the apical medium in the transwell system (FIG. 2A). This same concentration was highly cytotoxic to cells when incubated in a standard plate format (data not shown)

Example 2

Figure 2B:
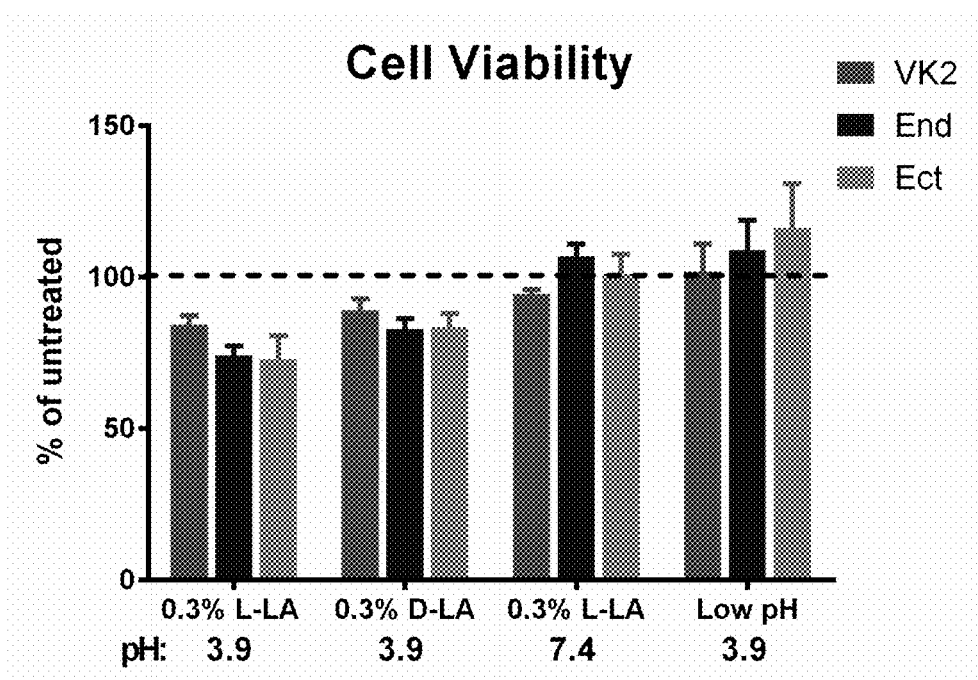
FIG. 2B shows the effect of 0.3% L-lactic acid (at low and neutral pH), 0.3% D-lactic acid and low pH alone (HCl) on viability of vaginal (VK2), endocervical (End) and ectocervical (Ect) epithelial cells. Mean and SEM shown from ≥23 independent experiments.

Concentrations of L-LA up to 0.3% had a minimal effect on the viability of VK2, epithelial cells (FIG. 2A). 0.3% L-LA and D-LA had a similar but very small effect on VK2, End and Ect cell viability, while 0.3% L-LA neutralised to pH 7.4 or low pH alone (adjusted to pH 3.9 with HCl) was non-toxic (FIG. 2B).

Example 3

Figure 3A:
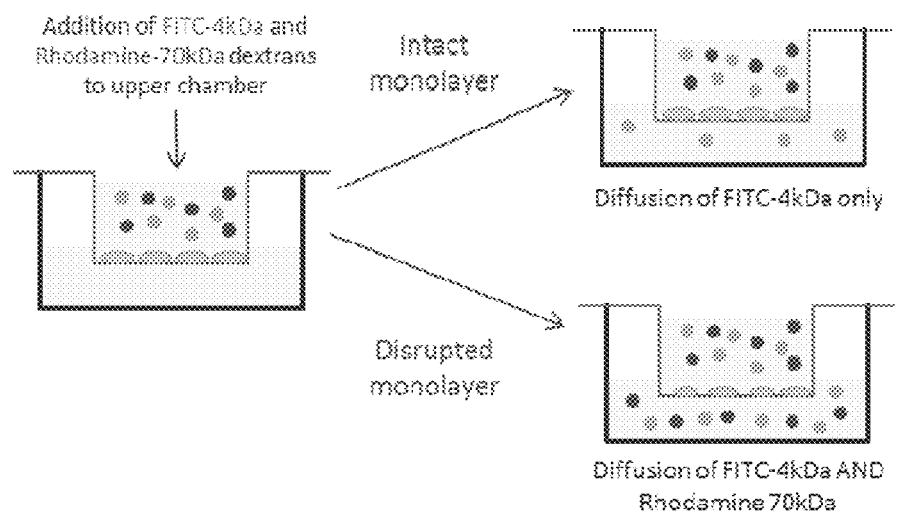
FIGS. 3A-D show an image (A) depicting the measurement of monolayer integrity via diffusion of 4 kDa-FITC (readily diffusible) and 70 kDa-Rhodamine (largely non-diffusible) dextrans as indicated, and a graphical representation of Epithelial cell monolayer integrity assessed by the addition of 2 mg/ml of FITC-labelled 4 kDa (B) or Rhodamine-labelled 70 kDa (C) dextran to the upper chamber of a transwell. Dextran diffusion rate measured by sampling basal chamber and detection of fluorescently labelled dextrans using the FLUOStar Optima. Diffusion of the dextrans over time across epithelial cells either untreated or cell treated with 0.3% L-lactic acid (L-lactic acid) is shown (D) Mean dextran diffusion rates (±SEM) at 3 h in VK2, End and Ect cells treated with 0.3% L-LA expressed as % of untreated cells from n=5 experiments.
Figure 3B:
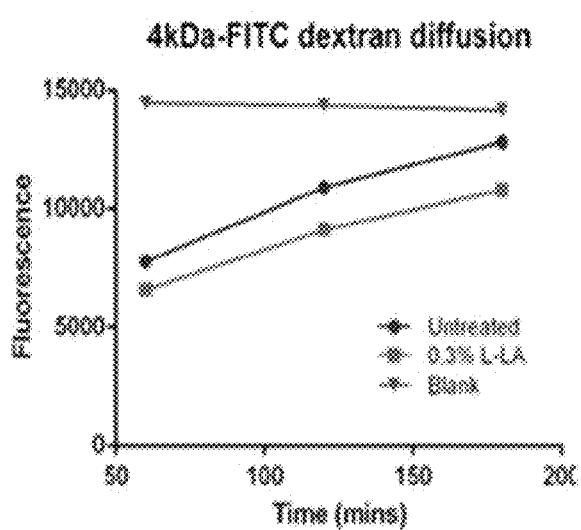
Figure 3C:
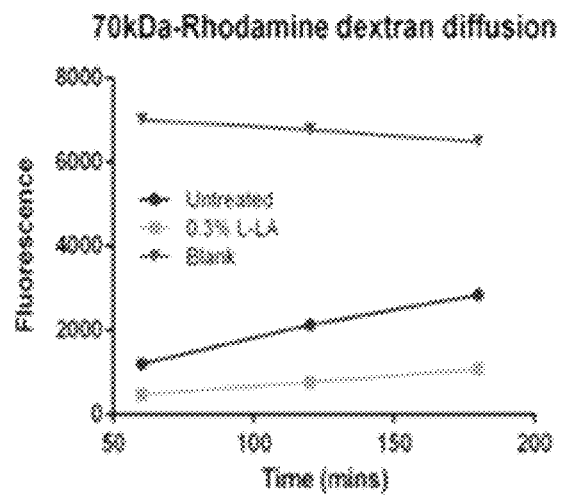
Figure 3D:
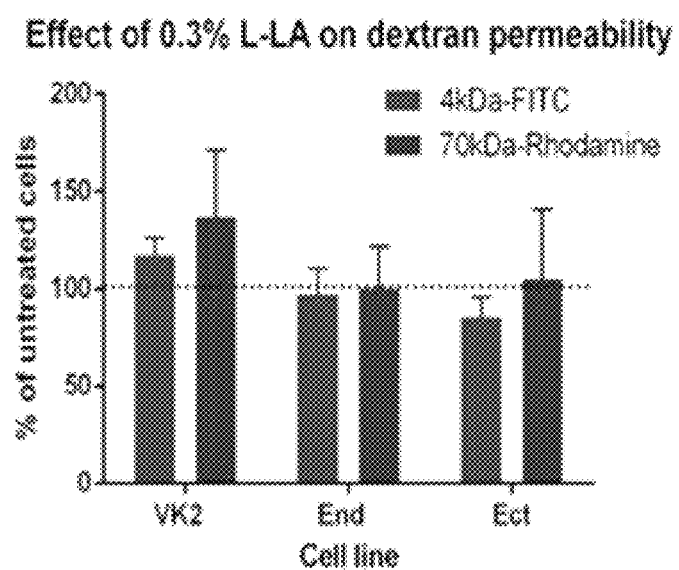

This model can also be used to determine the effect of acids on monolayer integrity (FIG. 3A) by measuring the diffusion rate of small (4 kDa, readily diffusible, FIG. 3B) and large (70 kDa, largely non-diffusible, FIG. 3C) fluorescently labelled dextrans across the epithelial monolayer. We show that 0.3% L-lactic acid (pH 3.9) does not markedly alter the permeability and thus monolayer integrity of the VK2, Ect or End cell lines (FIG. 3D). Thus, L-LA at near physiologic concentrations and pH does not affect viability or permeability of the VK2, or Ect or End cell lines cultured in transwells.

Virucidal, relatively non-toxic concentrations of L-LA (0.3%) elicit an anti-inflammatory response from epithelial cells of the FRT and reduce the pro-inflammatory response of cells to TLR-induced inflammation. D-LA had a similar anti-inflammatory effect, but L-LA at neutral pH nor low pH media alone did not. These results suggest the potential for LA to be used in topical microbicides to maintain an anti-inflammatory state in the FRT, and help reduce HIV susceptibility.

Example 4

An analysis was performed to determine if physiologic noncytotoxic concentrations of L-LA alter the release of immune modulators by VK2, End and Ect cells by incubating cells in transwells with L-LA for 24 h at 37° C. in serum free keratinocyte medium and harvesting supernatants (from the apical chamber) for release of immune modulators. 0.3% L-LA present in the apical medium reduces secretion of pro-inflammatory mediators IL-6 (FIG. 4A) and IL-8 (FIG. 4B) induced by the TLR3 agonist PIC by epithelial cells from the FRT. A similar trend was observed with the bacterial TLR agonists Pam3Ck (TLR2) and lipopolysaccharide (TLR4) in End and Ect cells (see FIG. 7 for data from End cells). These data show that L-LA significantly reduces IL-6 and IL-8 production from epithelial cells.

Example 5

Figure 5:
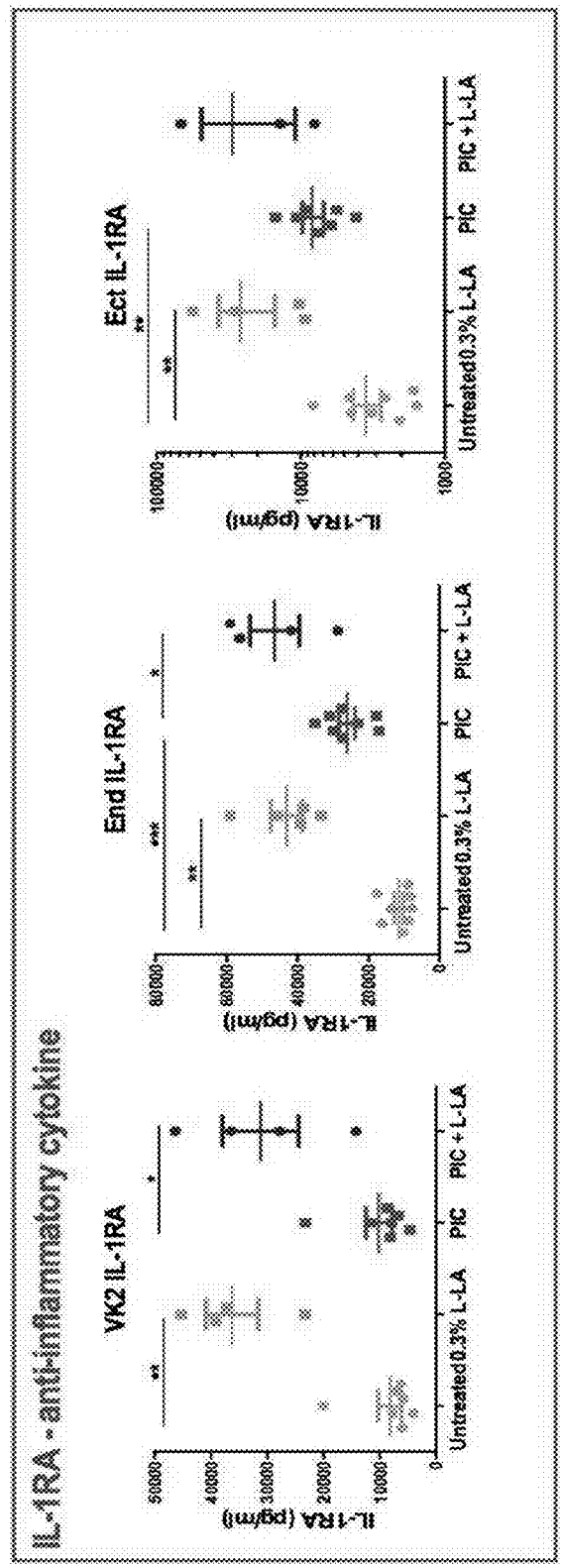
FIG. 5 is a graphical representation depicting that L-lactic acid (0.3%, pH 3.9) promotes induction of anti-inflammatory IL-1RA—irrespective of the presence of TLR agonist from VK2, End and Ect epithelial cells. *denotes p<0.05, p<0.01, *p<0.001 Data from n≥23 independent assays.

L-LA promotes the production of anti-inflammatory mediator, IL-1RA. Using similar culture conditions as in FIGS. 4A, B it was determined that 0.3% L-LA (pH 3.9)

induces IL-1RA production in VK2, End and Ect cell lines in the absence or presence of TLR3 agonist PIC (FIG. 5). The same result was obtained with bacterial TLR agonists Pam3Ck (TLR2) and lipopolysaccharide (TLR4) in all three cell lines (see FIGS. 7A-C for data from End cells). Taken together, these data show that lactobacilli in the lower FRT produce L-lactic acid that may have an anti-inflammatory effect and could play a critical role in preventing immune cell activation, recruitment and thus HIV infection in vivo.

Example 6

Figure 6:
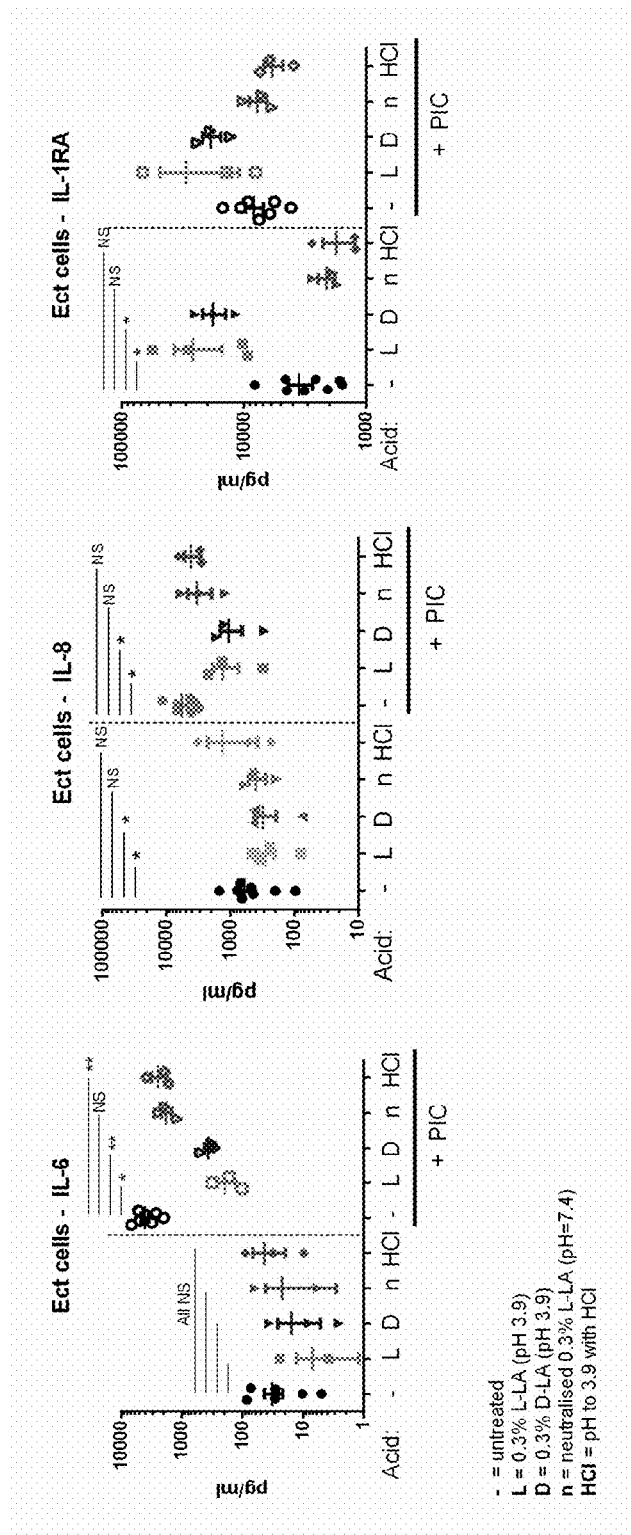
FIG. 6 is a graphical representation of the anti-inflammatory mediator effects (ie IL-1RA induction and inhibition of PIC-induced IL-6 and IL-8 production) on Ect epithelial cells observed with 0.3% L-(L) and D-lactic acid (D) pH 3.9 but not with neutralised L-lactic acid (n) or with media acidified to pH 3.9 with HCl alone (HCl). NS, not significant, * denotes p<0.05, p<0.01, *p<0.001. Data from n≥23.

Anti-inflammatory cytokine effects are mediated by L- and D-LA but not HCl or L-LA at neutral pH. L vs D-LA were evaluated at pH 3.9 and tested L-LA at pH 7.4 (FIG. 6) in Ect cells. It was also determined whether the effect being observed was due to LA or could be mediated by low pH alone by acidifying media to pH 3.9 with HCl. We found that both 0.3% L- and D-LA reduce secretion of pro-inflammatory mediators IL-6 and IL-8 induced by the TLR3 agonist PIC and increase IL-1RA production by Ect epithelial cells. However, neither neutralised L-LA nor HCl acidified media had any significant effect on decreasing levels of proinflammatory cytokines or increasing the production of the IL-1RA anti-inflammatory cytokine. A similar trend was observed with End and VK2 cells (data not shown). These data clearly show that the immune mediator effects of lactic acid is due to the protonated, uncharged form, can be observed with both lactic acid isomers found in the vagina, and is not simply due to acidity alone due to the inorganic acid, HCl.

Example 7

Methods for Examples 1-6
Cytokine Assay:
Cytokines were measured using FlowCytomix assays, utilising the basic reagents kit, in conjunction with simplex kits for IL-6, IL-8 and IL-1RA (eBiosciences).
Assays were carried out according to the manufactures instructions and standard operating procedures known to a person skilled in the art.
Preparation of Standards:
Reconstitution:
Pulse spin vials then reconstitute with the volume of dH$_2$O advised on the sample bottle.
Swirl vial to mix and wait 10-30 min before pipetting. Pulse spin tubes again before removing aliquot.
Preparing Standard Dilutions:
Add 10 µL of EACH standard in a final volume of 200 µL of 1× Assay buffer.
ie for 5 analytes, 5×10 µL of each standard+150 µL assay buffer.
NB can use 5 µL of each standard in final volume of 100 µL for S1 to conserve standard.
Add 100 µL of 1× assay buffer to 6 tubes labelled standards 2-7.
Transfer 50 µL of initial standard mixture (standard 1) to tube #2, mix well then transfer 50 µL of this to tube #3 etc.

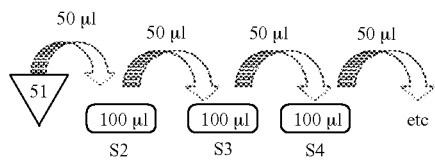

Preparation of Beads:
Require 15 µL beads/per test. Calculate number of test required (including standards, blank, plus one for set up) and ×15 µL to get volume of bead required (add 1 more test for pipetting).
Vortex each bead mix for 5 secs, pipette beads up and down and aliquot volume required. Need 1/20 total volume of beads for each bead set
ie. For 22 tests, need 330 µL beads so need 16.5 µL of each bead.
Fill volume of bead mixture up to final volume with reagent dilution buffer.
Centrifuge bead mix at 3000 g for 5 min, remove excess liquid leaving 50 µL s/n (ie if volume was 330 µL, remove 280 µL s/n).
Add the same volume of reagent dilution buffer as was removed and vortex mix for 5 secs.
Preparation of Biotin-conjugate Mix:
Require 30 µL of mix per test. Calculate volume required—number of test (plus extra for pipetting)×30 µL.
Pipette 1/20 of volume required of biotin-conjugate for each mix.
ie for 22 tests, need 660 µL mix and 33 µL of EACH biotin-conjugate.
Fill volume up to final volume with reagent dilution buffer.
Preparation of Streptavidin-PE Solution:
Require 30 µL of Streptavidin-PE per test. Calculate volume required ie number of tests (plus extra for pipetting)×30 µL.
Mix 1/31.25 the final volume of concentrated Streptavidin-PE and fill up to final volume with 1× assay buffer.
ie. For 22 tests, need 660 µL of 1× Streptavidin-PE, so 21.1 µL of concentrated Streptavidin-PE+639 µL of 1× assay buffer.
Test Procedure
1. Calculate required volumes of reagents and make standards, bead mixtures and biotin-conjugate as described above.
2. Add 15 µL of either standard, sample or blank (1× assay buffer) to appropriately labelled tubes.
3. Add 15 µL of prepared bead mixture to each tube.
4. Add 30 µL of biotin-conjugate mix to each tube, mix tubes well and incubate at room temp for 2 hours. Protect samples from light with foil.
5. Prepare Streptavidin-PE mix.
6. Add 0.6 ml 1× assay buffer to each tube and centrifuge at 200 g for 5 min.
7. Discard s/n, leaving approx. 100 µL. Repeat for a total of 2 washes.
8. Add 30 µL of Streptavidin-PE mix to all tubes, mix well and incubate at room temp for 1 hour (protected from light).
9. Add 0.6 ml 1× assay buffer to each tube and centrifuge at 200 g for 5 min.
10. Discard s/n, leaving approx. 100 µL. Repeat for a total of 2 washes.
11. Discard s/n from final wash, leaving 100-200 µL of buffer. Analyse samples on the flow cytometer within 24 hours (preferable the same day as the experiment).
Analysis on Flow Cytometer
Bead fluorescence is FL3 and analyte signal in FL2 (PE).
Use setup beads to set parameters before each experiment and standard 1 for final instrument settings.
Do not change voltage, compensation or flow rate during experiment.

Setup:
1. Prepare a vial of setup beads; vortex vial then pipette 500 μL beads into a labelled tube.
2. In setup mode, open a new protocol and create a dot plot window for FSC vs SSC (linear mode) and two windows of FL2 (PE) on x axis and FL3 (far red) on y axis (log mode).
3. Use setup beads to adjust FSC and SSC so both bead populations are visible. Gate the larger beads as R1 and the smaller population as R2.
4. Select R1 in the first dot plot and R2 in the second. Adjust FL2 voltage so beads are position in far left. Adjust FL3 voltage so bead populations are clearly separated.
5. Run standard 1. Adjust FL2 so the beads touch the right hand axis. If bead populations are not horizontal, increase FL3 compensation. Save settings.

Acquisition:
1. Switch to acquisition mode, and set up file name and save location (files should be xx.001, x.002).
2. Run samples and acquire 300 beads in R2 per analyte ie 5 analytes=1500 events.

Example 8

Methods for Examples 1-7
The effect of virucidal concentrations of L-LA on epithelial cells from the FRT was assessed using the vaginal (VK2), endocervical (End) and ectocervical (Ect) epithelial cell lines seeded into transwells.
Toxicity and epithelial monolayer integrity were determined by cell viability staining and diffusion of fluorescently labelled dextrans, respectively.
Cytokine release from cells stimulated for 24 h with toll-like receptor (TLR) in the absence or presence of L-LA was determined using a flow cytometry-based bead assay (FlowCytomix, eBiosciences).
The effect of D-LA and L-LA at neutral pH was also determined and compared to media pH adjusted to low pH with HCl.

Figure 7A:
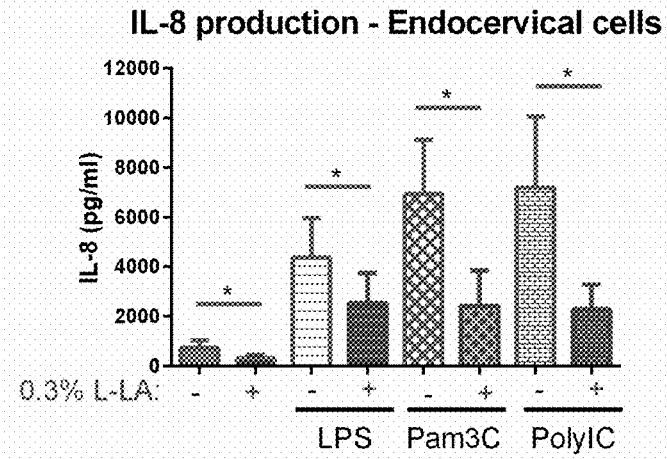
FIGS. 7A-C are a graphical representation depicting: Top panel: IL-8 (A), IL-6 (B) and IL-1RA (C) production from Endo cells after stimulation with the TLR agonists LPS (TLR4), Pam(3)CSK(4) (TLR1/TLR2) or Poly(I:C) (TLR3) for 24 h in the absence or presence of 0.3% L-lactic acid. Similar results were seen in VK2 and Ect cells. Mean and SEM shown from ≥3 independent assays. *=p<0.05, NS=Not statistically significant.
Figure 7B:
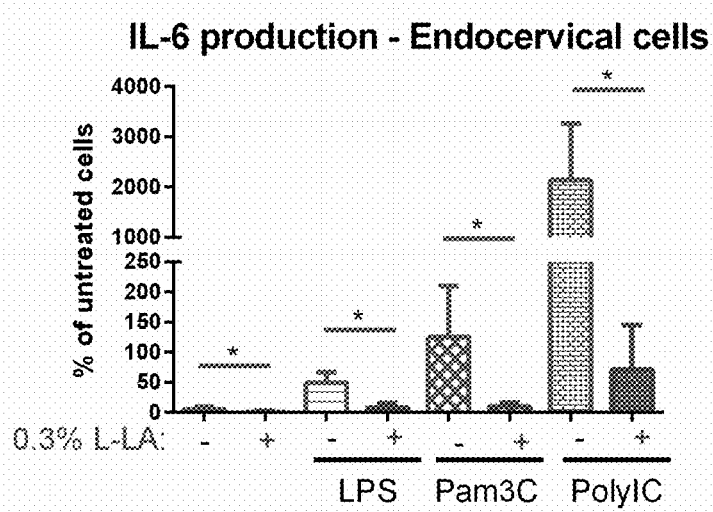
Figure 7C:
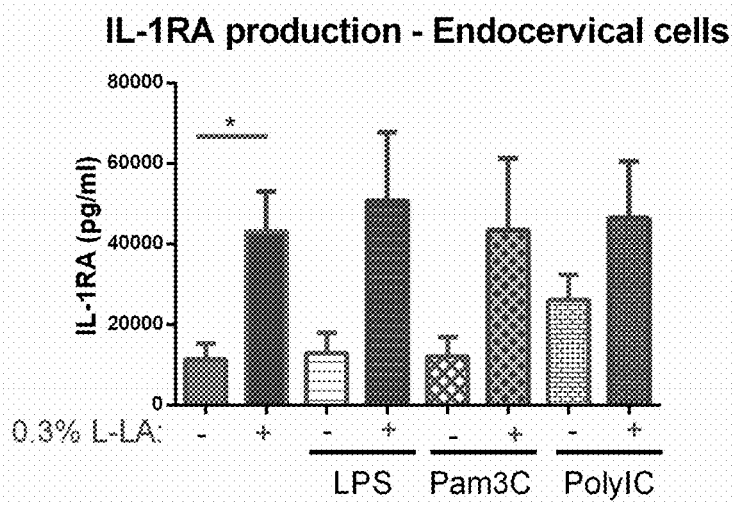
Figure 8A:
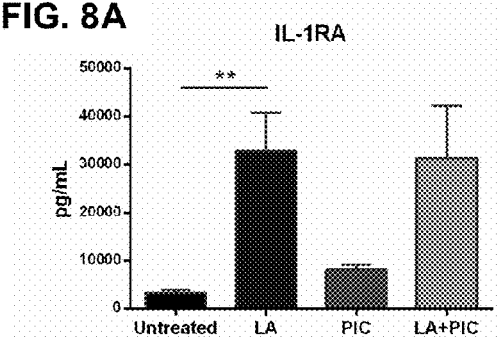
FIGS. 8A-F are a graphical representation depicting the production of the anti-inflammatory cytokine IL-1RA (A), and the pro-inflammatory cytokines IL-6 (B), IL-8 (C) and TNF (D) and the chemokines RANTES (E) and MIP3α (F) from Ect cells after stimulation with 0.3% LA, PIC or both as indicated. Graphs show mean and SEM from n≥4 independent experiments. * p<0.05,  p<0.01, * p<0.001. Similar data were obtained from VK2 and End epithelial cell lines.
Figure 8B:
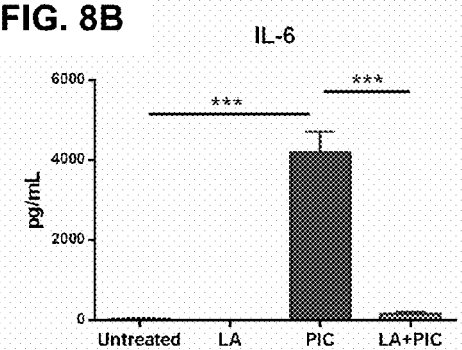
Figure 8C:
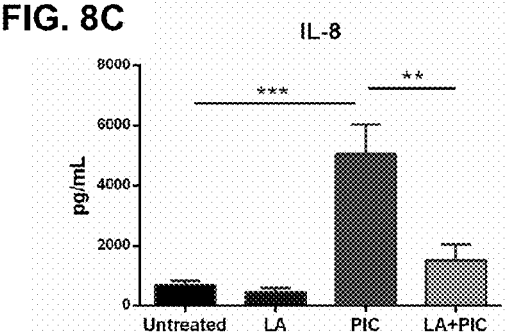
Figure 8D:
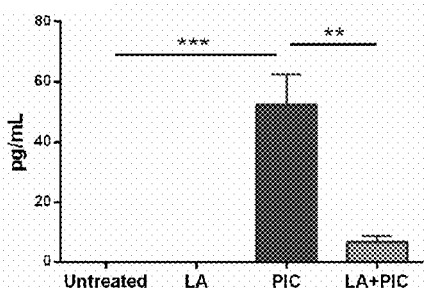
Figure 8E:
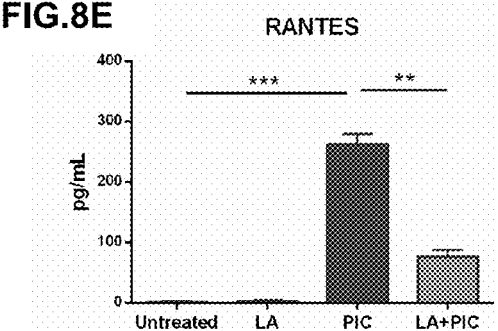
Figure 8F:
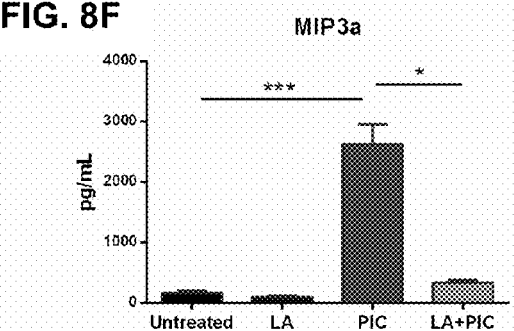
Figure 9A:
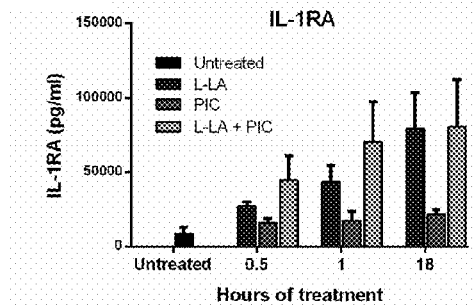
FIGS. 9A-F are a graphical representation depicting the Ect epithelial cells were stimulated with 0.3% LA, PIC or both for either 0.5, 1 or 18 hrs, and cytokine production measured in the culture supernatant at 18 hrs post stimulation. Production of the anti-inflammatory cytokine IL-1RA (A), and the pro-inflammatory cytokines IL-6 (B), IL-8 (C) and TNF (D) and the chemokines RANTES (E) and MIP3α (F) are shown. Graphs show mean and SEM from n=3 independent experiments. Similar data were obtained from VK2 epithelial cells
Figure 9B:
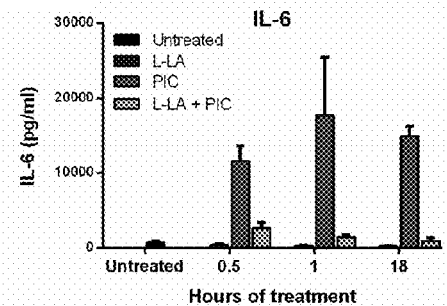
Figure 9C:
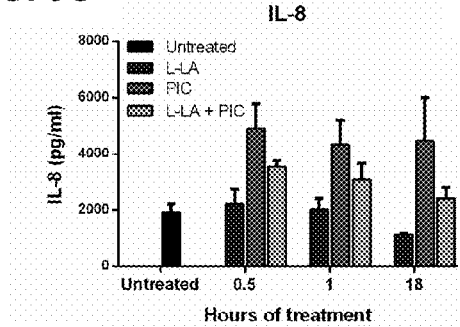
Figure 9D:
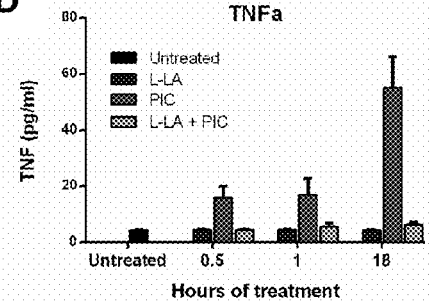
Figure 9E:
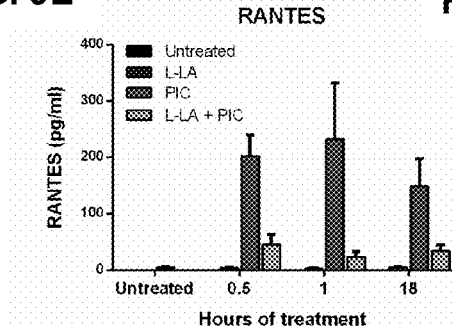
Figure 9F:
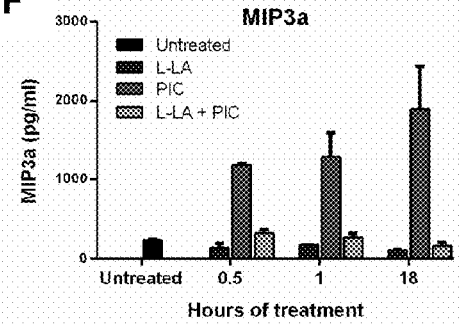
Figure 10A:
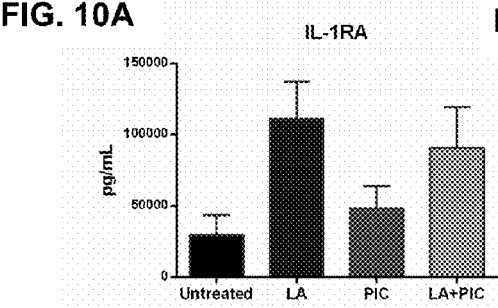
FIGS. 10A-F is a graphical representation depicting the production of the anti-inflammatory cytokine IL-1RA (A), and the pro-inflammatory cytokines IL-6 (B), IL-8 (C) and TNF (D) and the chemokines RANTES (E) and MIP3α (F) from primary vaginal epithelial cells after stimulation with 0.3% LA, PIC or both as indicated. Graphs show mean and SEM from n=4 independent experiments. * p<0.05, ** p<0.01.
Figure 10B:
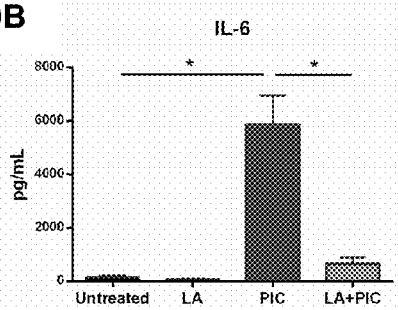
Figure 10C:
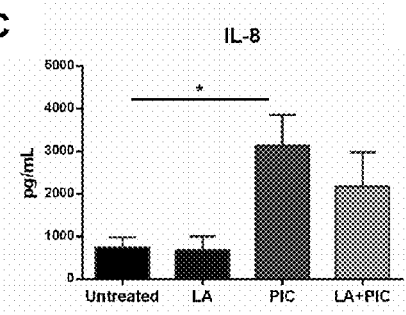
Figure 10D:
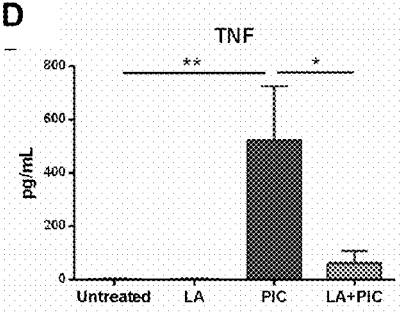
Figure 10E:
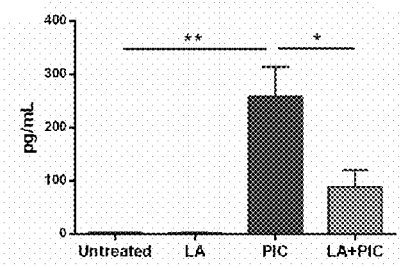
Figure 10F:
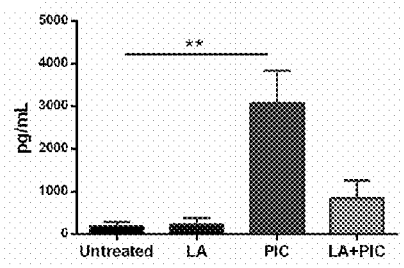

Results
L- and D-LA induce an anti-inflammatory state in FRT epithelial cells and inhibit the pro-inflammatory response to TLR agonists
Stimulation of epithelial cell lines with TLR2, 3 and 4 agonists induced the production of pro-inflammatory cytokines IL-8 and IL-6. (FIGS. 7A-C)

Example 9

Inflammatory Effects of L-Lactic Acid in the Presence of PIC on Epithelial Cells
Results
FIGS. 8A-F show that L-LA reduced the production of pro-inflammatory cytokines, IL-6 (B), IL-8 (C), TNFα (D), HIV-promoting chemokines RANTES (E) and MIP3α (F) induced by TLR agonists from lower FRT epithelial cells. L-LA induced a significant increase in anti-inflammatory cytokine, IL-1RA (A). This trend was seen with VK2 and Ect cells.

Example 10

Time Course of Inflammatory Effects of L-Lactic Acid in the Presence of PIC on Epithelial Cells
Results
To determine the minimum time required to elicit cytokine/chemokine production, cells were stimulated with PIC in the presence of absence of L-LA (as per FIGS. 9A-F) and cytokine production measured at 30 minutes, 1 hour and 18 hours.
FIGS. 9A-F demonstrate a 30 minute treatment of L-LA is sufficient for the production of anti-inflammatory cytokine, IL-RA (A) and pro-inflammatory cytokines, IL-6 (B), IL-8 (C), TNFα (D), HIV-promoting chemokines RANTES (E) and MIP3α (F) induced by TLR agonists from lower FRT epithelial cells. This trend was seen with VK2 and Ect1 cells.

Example 11

Inflammatory Effects of L-Lactic Acid in the Presence of PIC on Primary Ectocervical Cells
Culture of Human Primary Ectocervical Cells in Transwells.
Results
To further qualify the data in Example 9, we repeated the experiment with primary ectocervical cells. FIGS. 10A-F demonstrates a trend similar to that of LA treatment of cells lines with the production of anti-inflammatory cytokine, IL-1RA (A) and pro-inflammatory cytokines, IL-6 (B), IL-8 (C), TNFα (D), HIV-promoting chemokines RANTES (E) and MIP3α (F) induced by TLR agonists from lower FRT epithelial cells.

Example 1

Methods for Examples 1-11
Passaging and LA-treating Epithelial Cells from the Female Genital Tract
Cell Lines and Propagation
All cells are epithelial cells transformed with E6E7 from HPV-16

TABLE 1

Cell lines

| Source | Name | Cell type | ATCC ID |
| --- | --- | --- | --- |
| Vaginal | VK2/E6E7 | Epithelial | CRL-2616 |
| Endocervix | End/E6E7 | Epithelial | CRL-2615 |
| Ectocervix | Ect1/E6E7 | Epithelial | CRL-2614 |

Protocols for propagation and subculturing are provided on the ATCC website and are identical for all three cell types. The subculturing protocol used in the RBA lab is a slight modification of this and is listed below.

Media
Cells are grown in serum free keratinocyte media (Cat #17005-042 from Life Technologies) supplemented with the following per 100 ml media (Table 2.)

TABLE 2

Media supplement

| Supplement | Final Conc. | Volume/stock solution | Source |
| --- | --- | --- | --- |
| $CaCl_2$ | 0.4 mM | 40 μL of 1M stock | Lab stock (filter sterilised/ autoclaved) |

TABLE 2-continued

Media supplement

| Supplement | Final Conc. | Volume/stock solution | Source |
|---|---|---|---|
| Human recombinant EGF | 0.1 ng/ml | 0.3 µL of 35 ng/µl stock* | Supplied with media |
| Bovine pituitary extract | 0.05 mg/ml | 385 µL of 13 mg/ml stock* | Supplied with media |
| Pen/Strep | 50 U/ml Pen + 50 µg/ml strep | 500 µL of 10,000 U/µg per ml stock | Lab stock |

*Check stock concentrations on individual aliquots as they vary from batch to batch.

Passaging Cells

Cells should be passaged before they become confluent (at 50-80%).

Remove media and wash once with PBS.

Rinse cells with trypsin/EDTA (500 µL for a T25 flask) and discard.

Detach cells in 500 µL trypsin (for T25 flask) at 37° C. for required time.

Resuspend cells in 4.5 mL DMEM complete and perform cell count if required.

Pellet cells (500 g/5 min), remove s/n and resuspend cells in SFKM supplemented as above.

Seed/split cells as required (a 1:5 split typically last a week for an approx. 70% confluent flask). Cells can be grown in 5 mL SFKM per T25.

Seeding Cells for LA Treatment.

Transwells are used for LA treatments. Inserts are for 24 well plates and have a diameter of approx. 6 mm (ie the size of a 96 well plate well), and a pore size of 0.4 µM which is the smallest pore size available. Both BD (Cat #353495) and Corning (Cat #3413) inserts have been used and both have a high pore density (1×108 per cm2); a trial of the BD inserts with a lower pore density yielded poor results so avoid these. Larger transwell insert sizes can be used, with volumes/cell numbers below scaled up appropriately.

For seeding into transwells, add 500 µL media into the bottom reservoir and 100,000 cells in a volume of 200 µL media into the upper transwell reservoir (membrane are=0.33 cm² ie that of a 96 well plate).

Cells should be seeded then cultured for 7 days prior to LA treatment (change media on day 3 or 4 post seeding).

Perform all addition/wash steps involving eth transwells gentry to avoid disrupting the cell monolayer and never touch pipette tips to the transwell membrane.

For LA Treatment and Assessment of Toxicity/Membrane Permeability

Cytokine release, toxicity and membrane permeability can be assessed using the same transwell sample. Caveat: as membrane permeability is assessed after toxicity using this protocol, we cannot rule out that the 1.5 hr MTS treatment may affect membrane permeability, although if all samples are treated similarly it can be assumed that the effect is the same for all. Otherwise, duplicate transwells can be set up for toxicity/membrane permeability experiments.

Remove media from well and reservoir. Add 400 µL fresh SFKM to lower reservoir and 100 µL of appropriate LA or control-containing media (in SFKM) to upper well and incubate for designated period (typically 18-24 hr for cytokine production).

After incubation, remove s/n from upper reservoir and aliquot into appropriately labelled tubes and freeze at −80° C. for future cytokine analysis.

NB A sample of the media in the lower reservoir can also be stored for analysis. A small number of samples were used to compare the concentrations of cytokines in the upper and lower reservoirs after treatment and were found to be similar ie probably don't need to measure both.

Remove media from lower reservoir and wash both lower reservoir (500 µL/wash) and transwell (200 µL/wash) twice with PBS.

Add 400 µL fresh SKFM to lower reservoir and 100 µL of SFKM containing 18 µL MTS reagent to upper reservoir and incubate at 37° C. for up to 90 mins.

Remove 50-80 µL of MTS-containing media from upper transwell and transfer to a 96-well plate for analysis on plate reader. Read MTS at A490 nm (background at 320 nM).

Some volume of media from the upper reservoir is lost during the incubation, so don't try and transfer 100 µL as you will have unequal volumes from each well. 50-80 µL is adequate.

After MTS treatment, wash reservoir and transwell insert with PBS as described above.

Add 400 µL fresh SFKM to lower reservoir and 100 µL of SFKM containing 2 mg/ml final each of FITC labelled 4 kDa dextran (Sigma Cat #FD4, 100 mg) and Rhodamine labelled 70 kDa dextran (Sigma Cat #R9379, 100 mg).

Dextrans come as a powder and are dissolves in sterile PBS- to a concentration of 100 mg/ml. 2 µL of each dextran is required per well, but make a mastermix for all wells.

Incubate at 37° C. for 3 hours. A sample (50 µL) of media from the lower reservoir can be taken at 1, 2 and 3 hrs to examine the timecourse of uptake, otherwise take a single sample at 3 hrs after addition.

Analyse sample in white optical plates on the Fluorstar in Fluorescence mode.

Excitation/emission filters used for FITC and Rhodamine are 490/520 and 510/590 respectively.

Ensure correct leads are attached for fluorescence reading.

Allow machine to warm up for 10-15 min prior to using.

Treatment of FGT Cells with TLR Agonists

The following concentrations of TLR agonists (Table 3.) have been used to activate FGT cells either alone of added with LA-containing media for 18-24 hours.

TABLE 3

TLR agonists

| Agonist | Targets | Source/Cat # | Stock concentration | Treatment concentration |
|---|---|---|---|---|
| Pam3Cyk | TLR2 (via 1/2) | InvivoGen: tlrl-pms | 1 mg/ml | 1 µg/ml |
| Poly(I:C) | TLR3 | InvivoGen | 5 mg/ml | 20 µg/ml |
| Lipopolysaccharide (LPS) | TLR4 | Lab 4 | 1 mg/ml | 1 µg/ml |

Example 13

Assessing the Anti-inflammatory Potential of Lactic Acid Containing Gels

The Effect of Acid Excipients on Cell Viability and Cytokine Production

Cell Culture and Treatment Conditions

The human ectocervical epithelial cell line Ect1 E6/E7 was utilized for these experiments. Cells were cultured and treated in serum free keratinocyte media (SFKM) containing supplements as per ATCC recommendations. Cells were seeded in 6 mm transwell inserts at a density of 100,000 cells per well, and cultured for 7 days prior to treatment. Cells were treated in 100 μL of SFKM containing the relevant stimulus for 1 hour, before treatment media was removed and upper and lower chambers of the transwells were washed with PBS-, and fresh SFKM added. Cells were subsequently incubated for an addition 18 hours to allow cytokine production. Cytokine-containing supernatants were collected and stored at −80° C. for future analysis and cell viability assessed via MTS assay as per manufacturer's recommendations.

Cyto/chemokine analysis: Levels of relevant cyto/chemokines in cell culture supernatants was measured using the Procartaplex multiplex system with analysis on the BioRad Luminex Platform as per protocol. The following factors were measured: anti-inflammatory cytokine (IL-1RA), pro-inflammatory cytokines (IL-6, IL-8, TNF, IL-1β), and chemokine (RANTES, MIP3α).

Treatment agents: Table 4 details the LA-containing gels and excipient acids tested in this analysis. The 3 vaginal gels were very viscous, so were diluted ⅕ in SFKM and sterile filtered prior to use. Lactacyd was less viscous and could be diluted ½ in SFKM.

A 1% citric acid stock (in $H_2O$) was used to make treatment media. Benzoic acid is insoluble in water, thus a 2% solution was made in DMSO, sterile filtered and used for making treatment media.

Results

Toxicity

Figure 11:
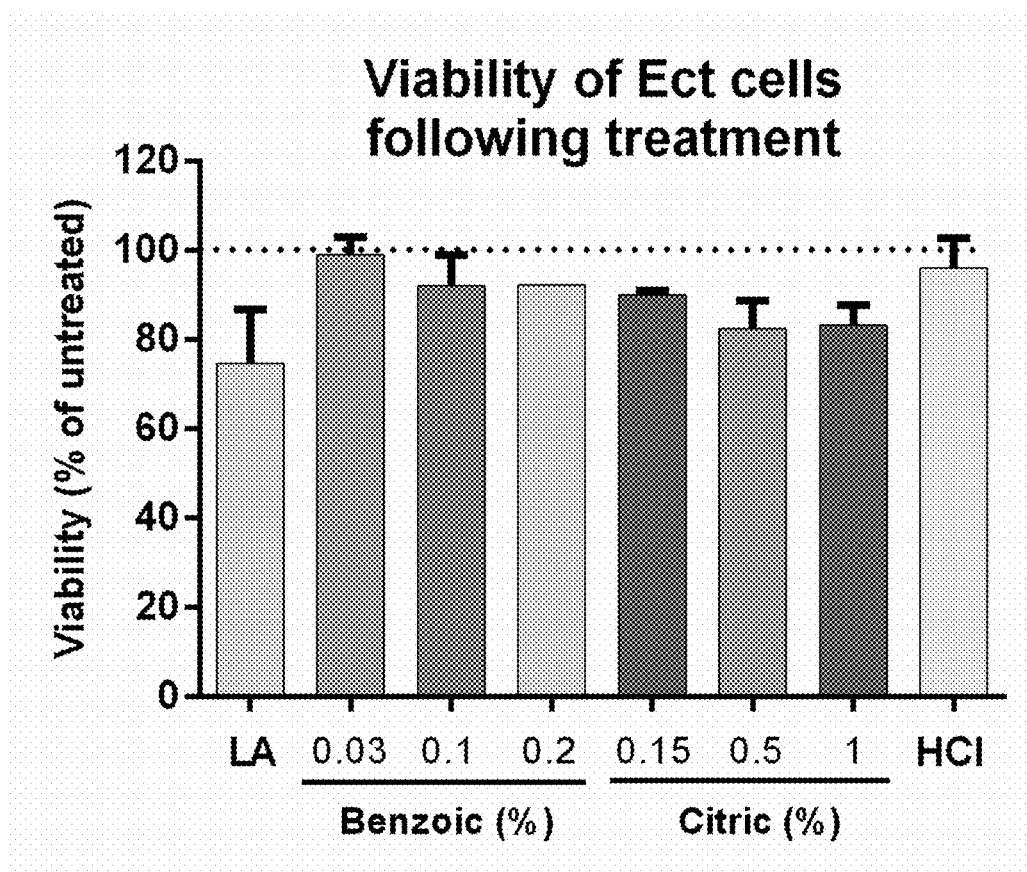
FIG. 11 is a graphical representation depicting the viability of Ect cells 18 hours after 1 hour incubation with the listed concentrations (%) of benzoic and citric acid. Viability of cells treated with LA and low pH alone (HCl) are shown for comparison. Data expressed as % viability as compared to untreated cells and are the mean and SD of 2 independent experiments (NB n=1 for 0.2% benzoic acid).

The viability of Ect epithelial cells following treatment with a range of concentrations of the excipients citric and benzoic acid was assessed. Neither benzoic nor citric acid had any significant effect on cell viability at the concentrations tested (FIG. 11). FIG. 11 demonstrates the viability of Ect cells 18 hours after 1 hour incubation with the listed concentrations (%) of benzoic and citric acid. Viability of cells treated with LA and low pH alone (HCl) are shown for comparison. Data expressed as % viability as compared to untreated cells and are the mean and SD of 2 independent experiments (NB n=1 for 0.2% benzoic acid). Note that dilutions of benzoic acid above 0.2% were insoluble.

Effect of Acids on Cytokine Production by Ect Cells

Figure 12A:
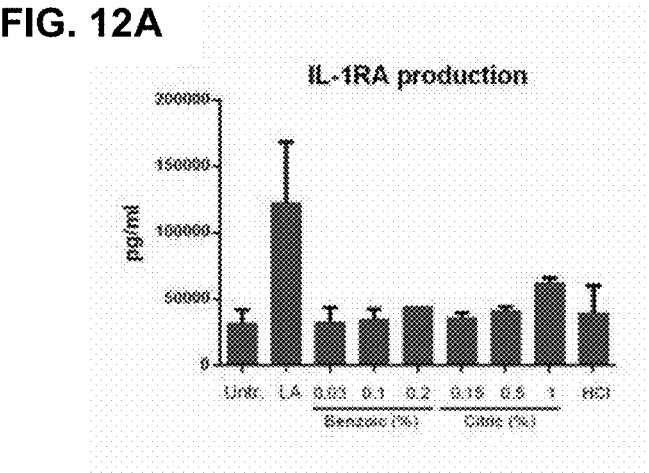
FIGS. 12A-C are a graphical representation depicting the production of IL-1RA (A) and IL-6 (B) from Ect epithelial cells following stimulation with the indicated concentrations of benzoic and citric acid for 1 hour as compared to untreated cells (Untr.) cells. Cells treated with LA or low pH 3.9 (HCl) are also shown. (C) Production of IL-1RA from Ect cells treated with LA in the absence of presence of 0.03% benzoic or 0.15% citric acid as indicated. Data shown are the mean and SD of n=2 experiments.
Figure 12B:
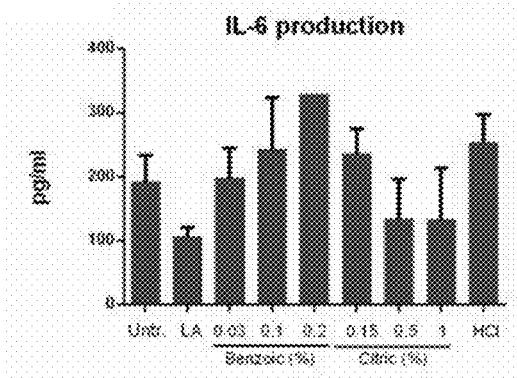

To determine whether the acid excipients themselves influenced the inflammatory state of Ect cells, levels of anti- and pro-inflammatory cytokines were measured in culture supernatants following treatment with various concentrations of benzoic or citric acid. Neither acid was associated with an altered expression of the anti-inflammatory agent IL-1RA (FIG. 12A) or the pro-inflammatory cytokine IL-6 (FIG. 12B). Levels of other immune mediators including IL-8, MIP3α, TNF, IL-1B and RANTES were similarly unaltered by treatment with these acids (not shown).

Effects of Acids on the Anti-inflammatory Actions of LA

Figure 12C:
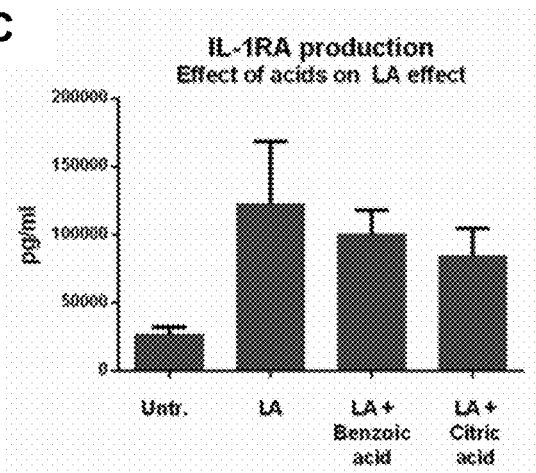
Figure 13A:
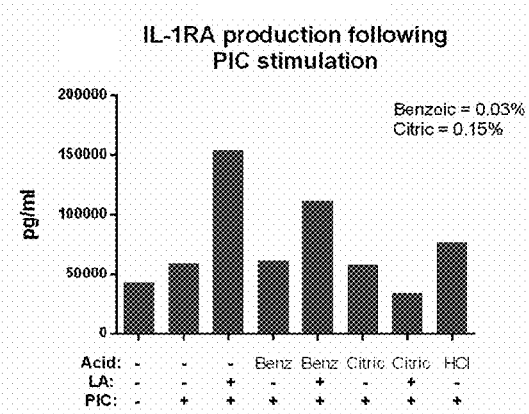
FIGS. 13A-D is a graphical representation depicting the production of the anti-inflammatory cytokine IL-1RA (A) and the pro-inflammatory cytokines IL-8 (B), IL-6 (C) and TNF (D) from Ect epithelial cells following stimulation with PIC for 1 hour in the presence of 0.3% LA and the presence or absence of benzoic or citric acid as indicated. Data shown are representative of n=2 experiments.
Figure 13B:
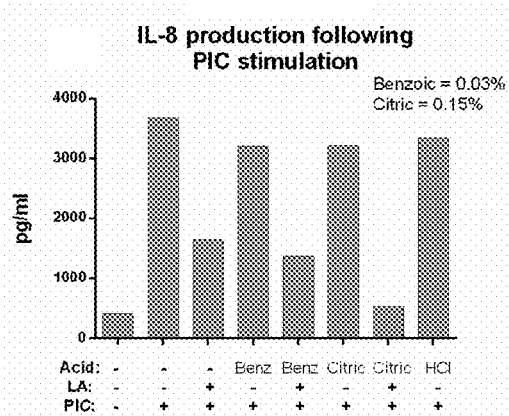
Figure 13C:
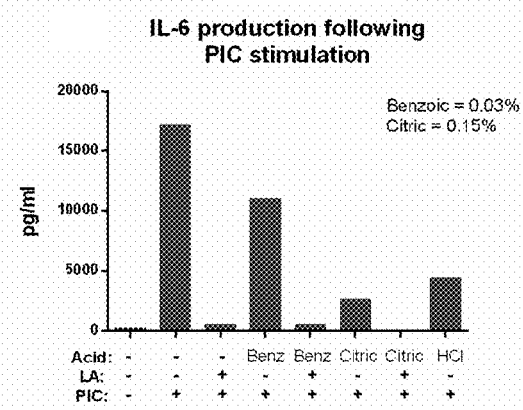
Figure 13D:
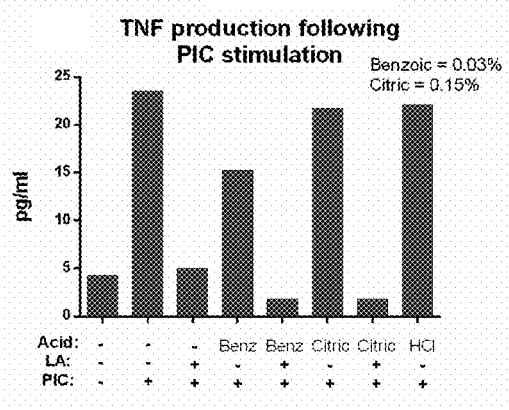

To determine whether the presence of benzoic or citric acid would interfere with the anti-inflammatory actions of LA, Ect cells were stimulated with LA in the absence or presence of 0.03% benzoic acid or 0.15% citric acid. These concentrations were selected as they represent the same ratio to LA as present in a dilution of Acidform containing 0.3% LA (see Table 4). FIG. 12C shows that although the presence of benzoic and citric acid at these concentrations was associated with slightly lower levels, the LA-induced production of IL-RA from Ect cells was largely preserved. Next,

TABLE 1

Feminine gels/products and acid excipients tested

| Product | Product details | [LA] | [LA] (in-house assay)# | Other ingredients | Dilution for ≈0.3% LA |
|---|---|---|---|---|---|
| LA-containin g gels: | | | | | |
| Caya | Vaginal gel | 5.5% | ≈8% | | ≈1/20 |
| Gynofit | Vaginal gel | Not stated | ≈1.5% | | ≈1/5 |
| Acidform | Vaginal gel | 2% (as per product insert) | ≈1.5% | 1% citric acid 0.2% benzoic acid | ≈1/5 |
| Lactacyd | Feminine wash | | ≈0.1% | | |
| Acids contained in LA-gels: | | | | | |
| Benzoic acid | Present in | | | | 0.03% |
| Citric acid | Acidform | | | | 0.15% |

Measured using an in vitro D/L-LA assay kit (Roche). No D-LA was detected.

NOTE: The pH of all treatment media containing gels/acids was adjusted to pH 3.9 (to match that of 0.3% LA) prior to treatment. This was performed to ensure that a similar concentration of protonated LA, the active form of LA, was compared. A pH control (media adjusted to pH 3.9 with HCl) was included to determine the effect of low pH alone.

Due to the poor buffering capacity of HCl, treatments containing HCl were refreshed every 20 min during the 1 hour treatment time to ensure the low pH of the treatment media was maintained.

we determined whether these concentrations of benzoic and acetic acid affected the ability of LA to block TLR-mediated inflammation. Ect cells were incubated with the TLR3 agonist Poly (I:C) (PIC) and LA in the absence or presence of 0.03% benzoic acid or 0.15% citric acid. The effect of benzoic and citric acid alone on the PIC-induced inflammatory response was also assessed. FIGS. 13A-D show that LA inhibits the PIC-induced production of the pro-inflammatory cytokines IL-8 (B), IL-6 (C) and TNF (D), and that this effect persists in the presence of either benzoic or citric acid. A similar trend was observed with the PIC-induced production of the chemokines RANTES and MIP3α (not shown). Benzoic and citric acid alone did not appear to alter PIC-induced cytokine production to a greater level that seen with low pH treatment alone (HCl). Whilst neither citric nor benzoic acid altered the production of IL-1RA (A) from cell stimulated with PIC, the presence of citric acid in combination with PIC and LA did result in a reduced production of the anti-inflammatory molecule IL-1RA as compared to cells stimulated with LA and PIC; the reproducibility and implications of this require further investigation.

Conclusion

Benzoic and citric acid, present as excipients in the vaginal gel Acidform, do not have a significant effect on the viability or inflammatory state (as indicated by cytokine production profile) of Ect epithelial cells.

Neither benzoic or citric acid, when present at a ratio equivalent to that found in Acidform gel, appear to significantly impair the anti-inflammatory actions of 0.3% LA.

These data cannot exclude the possibility that concentrations of benzoic (0.2%) and citric acid (1%) present in neat ACIDFORM may negate the anti-inflammatory effects of LA.

Figure 14:
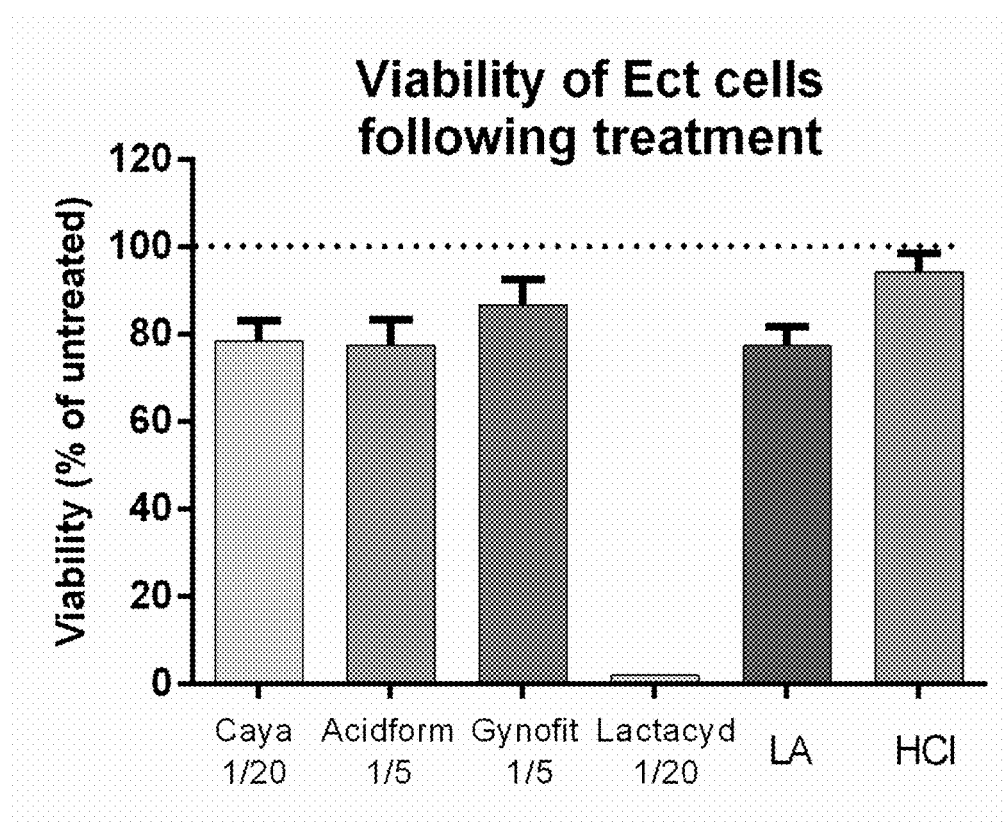
FIG. 14 is a graphical representation depicting the viability of Ect cells 18 hours after a 1 hour stimulation with the listed dilutions of LA-containing gels. Viability of cells treated with LA and low pH alone (HCl) are shown for comparison. Data expressed as % viability as compared to untreated cells and show mean and SEM from n=3 experiments.

Assessment of the Toxicity and Anti-inflammatory Effects of LA-containing Feminine Gels Toxicity The viability of Ect epithelial cells following treatment with dilutions of feminine hygiene products containing an LA concentration of approximately 0.3% (see Table 4) was assessed. The viability of cells treated with the diluted Caya, Gynofit and Acidform-containing media was similar to that of cells treated with 0.3% LA (FIG. 14). Treatment of cells with diluted Lactacyd resulted in cells detaching and being washed off the transwells. This product is actually a wash and is for external use only, thus analysis of the effects of this product were not analysed further.

Effect of Gels on Cytokine Production by Ect Cells

Figure 15A:
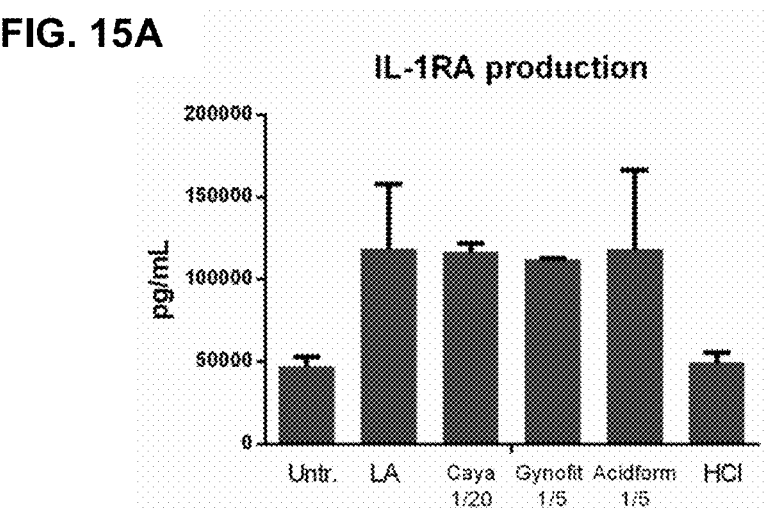
FIGS. 15A-B is a graphical representation depicting the production of IL-1RA (A) and IL-6 (B) from Ect epithelial cells following stimulation with diluted LA-containing gels for 1 hour. Cells treated with 0.3% LA or low pH (HCl) are also shown. Mean and SD are shown from 2 independent experiments.
Figure 15B:
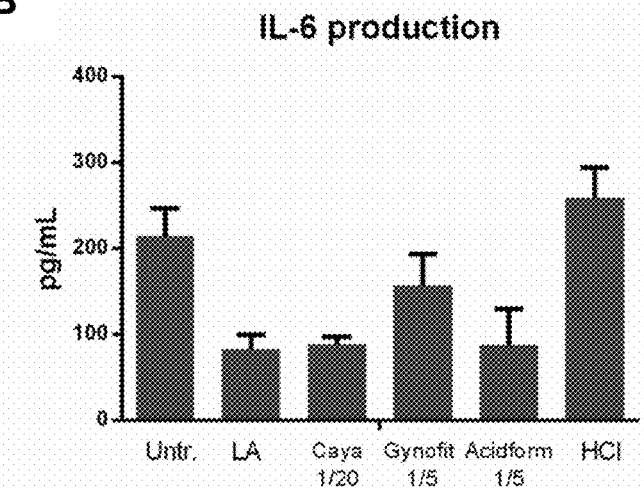

To determine whether the LA-containing gels were able to elicit a similar anti-inflammatory effect to that of LA alone, Ect cells were treated with the diluted gels and cytokine production measured. All 3 gels elicited increased production of the anti-inflammatory cytokine IL-1RA (FIG. 15A) to a similar extent to that seen with 0.3% LA alone. All gels were also able to reduce the basal production of the pro-inflammatory cytokine IL-6 to a level similar to that seen with LA alone (FIG. 15B), although the Gynofit gel showed a more subtle effect on IL-6 production. Both LA alone and LA-containing gels elicited a similar but small increase in production of the pro-inflammatory cytokine IL-1β, but levels were below the limit of detection of the assay (data not shown). There were no obvious differences in the production of other cytokines/chemokines (ie RANTES) between cells treated with LA-containing gels or LA alone (not shown).

Effect of LA-containing Gels on PIC-induced Inflammation

To determine whether LA-containing gels could inhibit the inflammatory response of PIC-induced cells to a similar extent to LA alone, cells were stimulated with PIC in the presence of absence of diluted gels (as per FIGS. 15A-B) and cytokine production measured. FIGS. 16A-F show that all 3 gels inhibited PIC-induced production of IL-6 (FIG. 16C), TNF (FIG. 16D), RANTES (FIG. 16E) and MIP3α (FIG. 16F) similar to that observed with LA alone, although for some cytokines (eg TNF) the Gynofit gel showed reduced activity as compared to Caya and Acidform. Acidform, and to a lesser extent Caya, also reduced PIC-mediated IL-8 (FIG. 16B) production.

Conclusion

The LA-containing feminine hygiene gels tested here required a significant dilution to achieve the physiological concentrations of LA which we have found to have anti-inflammatory properties.

The LA-containing gels, diluted to a concentration that is equivalent to 0.3% LA, do not significant toxicity and elicit a similar production of the anti-inflammatory factor IL-RA to LA alone.

Similar to LA alone, the LA-containing gels are able to inhibit the PIC-mediated production of inflammatory cytokines and chemokines for Ect cells, suggesting the LA contained in these agents retains its anti-inflammatory effect.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

Alexander et al, 2001, *J Endotoxin Res* 7:167-202

Blaskewicz, C. D., J. Pudney, and D. J. Anderson. 2011. Structure and function of intercellular junctions in human cervical and vaginal mucosal epithelia. *Biol Reprod* 85:97-104 (PMCID: PMC3123383)

Fichorova, R. N., and D. J. Anderson. 1999. Differential expression of immunobiological mediators by immortalized human cervical and vaginal epithelial cells. *Biol Reprod* 60:508-514. (PMID: 9916021)

Hickey, D. K., et al. 2011. Innate and adaptive immunity at mucosal surfaces of the female reproductive tract: stratification and integration of immune protection against the transmission of sexually transmitted infections. *J Reprod Immunol* 88:185-194. (PMID: 21353708)

Kaushic, C. 2011. HIV-1 infection in the female reproductive tract: role of interactions between HIV-1 and genital epithelial cells. *Am J Reprod Immunol* 65:253-260. (PMID: 21223427)

Keller, M. J., et al. 2012. Phase I randomized safety study of twice daily dosing of acidform vaginal gel: Candidate antimicrobial contraceptive. *Plos ONE* 7:e46901

Mirmonsef et al 2012, *Am J Rep Immunol* 67: 391

Mossop et al 2011, Influence of lactic acid on endogenous and viral RNA-induced immune mediator production by vaginal epithelial cells, *Obstet Gynecol* 118:840-6. (PMID: 21934447)

Pudney, J., A. J. Quayle, and D. J. Anderson. 2005. Immunological microenvironments in the human vagina and cervix: mediators of cellular immunity are concentrated in the cervical transformation zone. *Biol Reprod* 73:1253-1263. (PMID: 16093359)

Ulevitch, R. J. and Tobias P. S., 1999, Recognition of gram-negative bacteria and endotoxin by the innate immune system. *Curr Opin Immunol* 11:19-22. (PMID: 10047547)

Wira, C. R., K. S. Grant-Tschudy, and M. A. Crane-Godreau. 2005. Epithelial cells in the female reproductive tract: a central role as sentinels of immune protection. *Am J Reprod Immunol* 53:65-76. (PMID: 15790340)

We claim:

1. A method for down-regulating inflammation in the reproductive tract or genital tissue of a female mammal said method comprising mucosally administering a composition comprising an organic acid having the formula (I) or in vivo hydrolysable esters or phosphate esters and salts thereof (I):

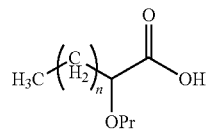

(I)

wherein n is an integer from 0 to 10;
wherein Pr is hydrogen or an in vivo hydrolysable protecting group; and
wherein the compound is in the form of a racemate, enantiomer or a mixture of enantiomers and wherein said mucosa is contacted with an effective concentration of approximately 0.1%-1.9% v/v of said organic acid.

2. A method of therapeutically or prophylactically treating a condition characterised by an aberrant, unwanted or otherwise inappropriate inflammatory response in the reproductive tract or the genital tissue of a female mammal said method comprising mucosally administering a composition comprising an organic acid having the formula (I) or in vivo hydrolysable esters or phosphate esters and salts thereof:

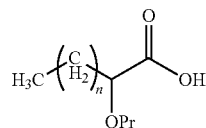

(I)

wherein n is an integer from 0 to 10;
wherein Pr is hydrogen or an in vivo hydrolysable protecting group; and
wherein the compound is in the form of a racemate, enantiomer or a mixture of enantiomers and wherein said mucosa is contacted with an effective concentration of approximately 0.1%-1.9% v/v of said organic acid.

3. The method according to claim 1 wherein said reproductive tract is the vagina and said genital tissue is the genital mucosa.

4. The method according to claim 1 wherein n is an integer from 0 to 5.

5. The method according to claim 4 wherein n is 0.

6. The method according to claim 5 wherein, n is 0 and Pr is hydrogen.

7. The method according to claim 1 wherein said organic acid is lactic acid.

8. The method according to claim 1 wherein, said composition does not comprise carboxylic acids other than the organic acid of formula (I).

9. The method according to claim 1 wherein, said composition comprises a concentration of 0.2% -1.8%, 0.3% -1.7%, 0.3% -1.6%, 0.3% -1.5%, 0.3% -1.4%, 0.3% -1.3%, 0.3% -1.2%, 0.3% -1.1% or 0.3% -1.0% v/v of the organic acid of formula (I).

10. The method according to claim 9 wherein said concentration is 0.2%, 0.3%, 0.4%,0.5%, 0.6%, 0.7%,0.8%, 0.9%, 1.0%, 1.1%, 1.2%, 1.3%, 1.4%, 1.5%, 1.6%, 1.7%, or 1.8% v/v.

11. The method according to claim 10 wherein said concentration is 0.3%, 0.4%, 0.5%, 0.6%, 0.7%, 0.8%, 0.9% or 1.0% v/v.

12. The method according to claim 1 wherein said composition is formulated together with a microbicide.

13. The method according to claim 1 wherein said inflammation is infectious vaginitis, atrophic vaginitis, irritant vaginitis, vaginosis or tissue injury.

14. A pharmaceutical composition comprising an organic acid having the formula (I) or in vivo hydrolysable esters or phosphate esters and salts thereof:

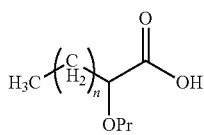

(I)

wherein n is an integer from 0 to 10;
wherein Pr is hydrogen or an in vivo hydrolysable protecting group; and
wherein the compound is in the form of a racemate, enantiomer or a mixture of enantiomers together with one or more pharmaceutically acceptable carriers and/or diluents.

15. The method of claim 1, wherein the organic acid having the formula (I) or in vivo hydrolysable esters or phosphate esters and salts thereof is coadministered with one or more other compounds.

* * * * *